(12) United States Patent
Nakamura et al.

(10) Patent No.: US 8,575,099 B2
(45) Date of Patent: Nov. 5, 2013

(54) AGENT FOR TREATING POLYGLUTAMINE AGGREGATION-CAUSED DISEASE OR SUPPRESSING ONSET THEREOF

(75) Inventors: Toshikazu Nakamura, Suita (JP); Hiroshi Funakoshi, Suita (JP); Daisuke Miyazawa, Nagoya (JP); Kunio Iwatani, Toyonaka (JP)

(73) Assignees: Osaka University, Osaka (JP); Kringle Pharma Inc., Osaka (JP)

( * ) Notice: Subject to any disclaimer, the term of this patent is extended or adjusted under 35 U.S.C. 154(b) by 392 days.

(21) Appl. No.: 12/226,447

(22) PCT Filed: Mar. 30, 2007

(86) PCT No.: PCT/JP2007/057218
§ 371 (c)(1),
(2), (4) Date: Jan. 30, 2009

(87) PCT Pub. No.: WO2007/122976
PCT Pub. Date: Nov. 1, 2007

(65) Prior Publication Data
US 2010/0168003 A1    Jul. 1, 2010

(30) Foreign Application Priority Data
Apr. 20, 2006 (JP) ................................. 2006-116635

(51) Int. Cl.
*A61K 38/18* (2006.01)
*C07K 14/47* (2006.01)

(52) U.S. Cl.
USPC .............................. 514/9.5; 424/9.1; 424/450

(58) Field of Classification Search
None
See application file for complete search history.

(56) References Cited

U.S. PATENT DOCUMENTS

| | | | | |
|---|---|---|---|---|
| 5,342,831 A * | 8/1994 | Nakamura et al. | ............. | 514/7.6 |
| 5,652,225 A * | 7/1997 | Isner | .................... | 514/44 R |
| 5,658,742 A | 8/1997 | Higashio et al. | | |
| 5,776,464 A * | 7/1998 | Nakamura | ................. | 424/198.1 |
| 5,840,311 A * | 11/1998 | Nakamura et al. | ........ | 424/198.1 |
| 6,036,972 A * | 3/2000 | Nakamura et al. | ............ | 424/422 |
| 6,303,126 B1 * | 10/2001 | Nakamura et al. | ........ | 424/198.1 |
| 6,699,837 B2 * | 3/2004 | Nakamura | .................... | 514/7.6 |
| 6,756,358 B2 * | 6/2004 | Iwamoto et al. | ................ | 514/7.6 |
| 7,507,401 B2 * | 3/2009 | Nakamura | ................... | 424/85.1 |
| 7,563,768 B2 * | 7/2009 | Nakamura et al. | ............. | 514/1.1 |
| 7,618,614 B2 * | 11/2009 | Tada et al. | ..................... | 424/9.1 |
| 7,696,170 B2 * | 4/2010 | Amano et al. | ................. | 514/9.5 |
| 7,838,494 B2 * | 11/2010 | Kubo et al. | .................... | 530/350 |
| 2003/0176347 A1 * | 9/2003 | Nakamura et al. | .............. | 514/12 |
| 2004/0265283 A1 * | 12/2004 | Morishita | .................. | 424/93.21 |
| 2006/0199762 A1 | 9/2006 | Nakamura et al. | | |
| 2006/0241074 A1 | 10/2006 | Woolf et al. | | |
| 2007/0015154 A1 | 1/2007 | Hedge et al. | | |
| 2007/0021335 A1 * | 1/2007 | Takeo et al. | ..................... | 514/12 |
| 2007/0026409 A1 | 2/2007 | Woolf et al. | | |
| 2010/0322998 A1 | 12/2010 | Nakamura et al. | | |

FOREIGN PATENT DOCUMENTS

| | | |
|---|---|---|
| EP | 0 672 685 | 9/1995 |
| WO | 03/016475 | 2/2003 |
| WO | 2005/023287 | 3/2005 |
| WO | 2005/034985 | * 4/2005 |

OTHER PUBLICATIONS

K. Matsumoto, "HGF ni yoru Chusu Shinkei Sonsho Shikkan ni Taisuru Saisei Chiryo no Kaihatsuteki Kenkyu", Chusu Shinkeikei no Shufuku Kino no Kaimei to Chiryo Oyo ni Kansuru kaihatsuteki Kenkyu Heisei 12 to 14 Nendo Kenkyu Hokokusho, 2003, pp. 31-34, along with a partial English translation thereof.

N. Ishihara et al., "Inhibition of apoptosis-inducing factor translocation is involved in protective effects of hepatocyte growth factor against excitotoxic cell death in cultured hippocampal neurons", Journal of Neurochemistry, vol. 95, No. 5, pp. 1277-1286, 2005.

Extended European Search Report issued Mar. 5, 2012 in corresponding European Application No. 07740654.4.

Sun, Woong, et al., "Overexpression of HGF Disease Progression and Prolongs Life Span in a Transgenic Mouse Model of ALS", The Journal of Neuroscience, vol. 22, No. 15, Aug. 1, 2002, pp. 6537-6548.

Friedlander, Robert M., "Apoptosis and Caspases in Neurodegenerative Diseases", The New England Journal of Medicine, vol. 348, 2003, pp. 1365-1375.

European Office Action issued Dec. 6, 2012 in corresponding European Application No. 07 740 654.4.

\* cited by examiner

*Primary Examiner* — John Ulm
(74) *Attorney, Agent, or Firm* — Wnderoth, Lind & Ponack, L.L.P.

(57) ABSTRACT

The present invention discloses an agent for treating a polyglutamine aggregation-caused disease or suppressing its onset, which comprises, as an active ingredient, (1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition.

15 Claims, 14 Drawing Sheets

SEQUENCE LISTING

<160> NUMBER OF SEQ ID NOS: 7

<210> SEQ ID NO 1
<211> LENGTH: 2187
<212> TYPE: DNA
<213> ORGANISM: Homo sapiens

<400> SEQUENCE: 1

| | | | | | |
|---|---|---|---|---|---|
| atgtgggtga | ccaaactcct | gccagccctg | ctgctgcagc | atgtcctcct | gcatctcctc | 60 |
| ctgctcccca | tcgccatccc | ctatgcagag | ggacaaagga | aaagaagaaa | tacaattcat | 120 |
| gaattcaaaa | aatcagcaaa | gactacccta | atcaaaatag | atccagcact | gaagataaaa | 180 |
| accaaaaaag | tgaatactgc | agaccaatgt | gctaatagat | gtactaggaa | taaaggactt | 240 |
| ccattcactt | gcaaggcttt | tgttttgat | aaagcaagaa | acaatgcct | ctggttcccc | 300 |
| ttcaatagca | tgtcaagtgg | agtgaaaaaa | gaatttggcc | atgaatttga | cctctatgaa | 360 |
| aacaaagact | acattagaaa | ctgcatcatt | ggtaaaggac | gcagctacaa | gggaacagta | 420 |
| tctatcacta | gagtggcat | caaatgtcag | ccctggagtt | ccatgatacc | acacgaacac | 480 |
| agcttttgc | cttcgagcta | tcggggtaaa | gacctacagg | aaaactactg | tcgaaatcct | 540 |
| cgaggggaag | aagggggacc | ctggtgtttc | acaagcaatc | cagaggtacg | ctacgaagtc | 600 |
| tgtgacattc | ctcagtgttc | agaagttgaa | tgcatgacct | gcaatgggga | gagttatcga | 660 |
| ggtctcatgg | atcatacaga | atcaggcaag | atttgtcagc | gctgggatca | tcagacacca | 720 |
| caccggcaca | aattcttgcc | tgaaagatat | cccgacaagg | gctttgatga | taattattgc | 780 |
| cgcaatcccg | atggccagcc | gaggccatgt | tgctatactc | ttgaccctca | cacccgctgg | 840 |
| gagtactgtg | caattaaaac | atgcgctgac | aatactatga | atgacactga | tgttcctttg | 900 |
| gaaacaactg | aatgcatcca | aggtcaagga | gaaggctaca | gggcactgt | caataccatt | 960 |
| tggaatggaa | ttccatgtca | gcgttgggat | tctcagtatc | ctcacgagca | tgacatgact | 1020 |
| cctgaaaatt | tcaagtgcaa | ggacctacga | gaaaattact | gccgaaatcc | agatgggtct | 1080 |
| gaatcaccct | ggtgttttac | cactgatcca | aacatccgag | ttggctactg | ctcccaaatt | 1140 |
| ccaaactgtg | atatgtcaca | tggacaagat | tgttatcgtg | ggaatggcaa | aaattatatg | 1200 |
| ggcaacttat | cccaaacaag | atctggacta | acatgttcaa | tgtgggacaa | gaacatggaa | 1260 |
| gacttacatc | gtcatatctt | ctgggaacca | gatgcaagta | agctgaatga | gaattactgc | 1320 |
| cgaaatccag | atgatgatgc | tcatggaccc | tggtgctaca | cggaaatcc | actcattcct | 1380 |
| tgggattatt | gccctatttc | tcgttgtgaa | ggtgatacca | cacctacaat | agtcaattta | 1440 |
| gaccatcccg | taatatcttg | tgccaaaacg | aaacaattgc | gagttgtaaa | tgggattcca | 1500 |
| acacgaacaa | acataggatg | gatggttagt | ttgagataca | gaaataaaca | tatctgcgga | 1560 |
| ggatcattga | taaaggagag | ttgggttctt | actgcacgac | agtgtttccc | ttctcgagac | 1620 |
| ttgaaagatt | atgaagcttg | gcttggaatt | catgatgtcc | acggaagagg | agatgagaaa | 1680 |
| tgcaaacagg | ttctcaatgt | ttcccagctg | gtatatggcc | ctgaaggatc | agatctggtt | 1740 |
| ttaatgaagc | ttgccaggcc | tgctgtcctg | gatgattttg | ttagtacgat | tgatttacct | 1800 |
| aattatggat | gcacaattcc | tgaaaagacc | agttgcagtg | tttatggctg | gggctacact | 1860 |
| ggattgatca | actatgatgg | cctattacga | gtggcacatc | tctatataat | gggaaatgag | 1920 |
| aaatgcagcc | agcatcatcg | agggaaggtg | actctgaatg | agtctgaaat | atgtgctggg | 1980 |
| gctgaaaaga | ttggatcagg | accatgtgag | ggggattatg | gtggcccact | tgtttgtgag | 2040 |

-continued

| | |
|---|---|
| caacataaaa tgagaatggt tcttggtgtc attgttcctg gtcgtggatg tgccattcca | 2100 |
| aatcgtcctg gtattttttgt ccgagtagca tattatgcaa aatggataca caaaattatt | 2160 |
| ttaacatata aggtaccaca gtcatag | 2187 |

<210> SEQ ID NO 2
<211> LENGTH: 2172
<212> TYPE: DNA
<213> ORGANISM: Homo sapiens

<400> SEQUENCE: 2

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa atcagcaaa gactacccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgtttttgat aaagcaagaa aacaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| agctatcggg gtaaagacct acaggaaaac tactgtcgaa atcctcgagg ggaagaaggg | 540 |
| ggaccctggt gtttcacaag caatccagag gtacgctacg aagtctgtga cattcctcag | 600 |
| tgttcagaag ttgaatgcat gacctgcaat ggggagagtt atcgaggtct catggatcat | 660 |
| acagaatcag gcaagatttg tcagcgctgg gatcatcaga caccacaccg gcacaaattc | 720 |
| ttgcctgaaa gatatcccga caagggcttt gatgataatt attgccgcaa tcccgatggc | 780 |
| cagccgaggc catggtgcta tactcttgac cctcacaccc gctgggagta ctgtgcaatt | 840 |
| aaaacatgcg ctgacaatac tatgaatgac actgatgttc ctttggaaac aactgaatgc | 900 |
| atccaaggtc aaggagaagg ctacagggc actgtcaata ccatttggaa tggaattcca | 960 |
| tgtcagcgtt gggattctca gtatcctcac gagcatgaca tgactcctga aaatttcaag | 1020 |
| tgcaaggacc tacgagaaaa ttactgccga aatccagatg ggtctgaatc accctggtgt | 1080 |
| tttaccactg atccaaacat ccgagttggc tactgctccc aaattccaaa ctgtgatatg | 1140 |
| tcacatggac aagattgtta tcgtgggaat ggcaaaaatt atatgggcaa cttatcccaa | 1200 |
| acaagatctg gactaacatg ttcaatgtgg gacaagaaca tggaagactt acatcgtcat | 1260 |
| atcttctggg aaccagatgc aagtaagctg aatgagaatt actgccgaaa tccagatgat | 1320 |
| gatgctcatg gaccctggtg ctacacggga aatccactca ttccttggga ttattgccct | 1380 |
| atttctcgtt gtgaaggtga taccacacct acaatagtca atttagacca tcccgtaata | 1440 |
| tcttgtgcca aaacgaaaca attgcgagtt gtaaatggga ttccaacacg aacaaacata | 1500 |
| ggatggatgg ttagtttgag atacagaaat aaacatatct gcggaggatc attgataaag | 1560 |
| gagagttggg ttcttactgc acgacagtgt ttcccttctc gagacttgaa agattatgaa | 1620 |
| gcttggcttg gaattcatga tgtccacgga agaggagatg agaaatgcaa acaggttctc | 1680 |
| aatgtttccc agctggtata tggccctgaa ggatcagatc tggttttaat gaagcttgcc | 1740 |
| aggcctgctg tcctgatga ttttgttagt acgattgatt tacctaatta tggatgcaca | 1800 |
| attcctgaaa agaccagttg cagtgtttat ggctggggct acactggatt gatcaactat | 1860 |
| gatggcctat tacgagtggc acatctctat ataatgggaa atgagaaatg cagccagcat | 1920 |
| catcgaggga aggtgactct gaatgagtct gaaatatgtg ctggggctga aaagattgga | 1980 |

-continued

```
tcaggaccat gtgagggga ttatggtggc ccacttgttt gtgagcaaca taaaatgaga    2040
atggttcttg gtgtcattgt tcctggtcgt ggatgtgcca ttccaaatcg tcctggtatt    2100
tttgtccgag tagcatatta tgcaaaatgg atacacaaaa ttattttaac atataaggta    2160
ccacagtcat ag                                                        2172
```

<210> SEQ ID NO 3
<211> LENGTH: 728
<212> TYPE: PRT
<213> ORGANISM: Homo sapiens

<400> SEQUENCE: 3

```
Met Trp Val Thr Lys Leu Leu Pro Ala Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
```

```
                    340             345             350
Tyr Cys Arg Asn Pro Asp Gly Ser Glu Ser Pro Trp Cys Phe Thr Thr
            355                 360                 365
Asp Pro Asn Ile Arg Val Gly Tyr Cys Ser Gln Ile Pro Asn Cys Asp
        370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
            420                 425                 430
Ser Lys Leu Asn Glu Asn Tyr Cys Arg Asn Pro Asp Asp Ala His
        435                 440                 445
Gly Pro Trp Cys Tyr Thr Gly Asn Pro Leu Ile Pro Trp Asp Tyr Cys
        450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
Asn Gly Ile Pro Thr Arg Thr Asn Ile Gly Trp Met Val Ser Leu Arg
            500                 505                 510
Tyr Arg Asn Lys His Ile Cys Gly Gly Ser Leu Ile Lys Glu Ser Trp
        515                 520                 525
Val Leu Thr Ala Arg Gln Cys Phe Pro Ser Arg Asp Leu Lys Asp Tyr
        530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                565                 570                 575
Ser Asp Leu Val Leu Met Lys Leu Ala Arg Pro Ala Val Leu Asp Asp
            580                 585                 590
Phe Val Ser Thr Ile Asp Leu Pro Asn Tyr Gly Cys Thr Ile Pro Glu
        595                 600                 605
Lys Thr Ser Cys Ser Val Tyr Gly Trp Gly Tyr Thr Gly Leu Ile Asn
        610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                645                 650                 655
Ile Cys Ala Gly Ala Glu Lys Ile Gly Ser Gly Pro Cys Glu Gly Asp
            660                 665                 670
Tyr Gly Gly Pro Leu Val Cys Glu Gln His Lys Met Arg Met Val Leu
        675                 680                 685
Gly Val Ile Val Pro Gly Arg Gly Cys Ala Ile Pro Asn Arg Pro Gly
        690                 695                 700
Ile Phe Val Arg Val Ala Tyr Tyr Ala Lys Trp Ile His Lys Ile Ile
705                 710                 715                 720
Leu Thr Tyr Lys Val Pro Gln Ser
                725

<210> SEQ ID NO 4
<211> LENGTH: 723
<212> TYPE: PRT
<213> ORGANISM: Homo sapiens
```

-continued

```
<400> SEQUENCE: 4

Met Trp Val Thr Lys Leu Leu Pro Ala Leu Leu Gln His Val Leu
1               5                   10                  15

Leu His Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
                115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
                180                 185                 190

Tyr Glu Val Cys Asp Ile Pro Gln Cys Ser Glu Val Glu Cys Met Thr
                195                 200                 205

Cys Asn Gly Glu Ser Tyr Arg Gly Leu Met Asp His Thr Glu Ser Gly
210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
                260                 265                 270

Thr Arg Trp Glu Tyr Cys Ala Ile Lys Thr Cys Ala Asp Asn Thr Met
                275                 280                 285

Asn Asp Thr Asp Val Pro Leu Glu Thr Thr Glu Cys Ile Gln Gly Gln
                290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
                340                 345                 350

Asp Gly Ser Glu Ser Pro Trp Cys Phe Thr Thr Asp Pro Asn Ile Arg
                355                 360                 365

Val Gly Tyr Cys Ser Gln Ile Pro Asn Cys Asp Met Ser His Gly Gln
        370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415
```

| | | | | | | | | | | | | |
|---|---|---|---|---|---|---|---|---|---|---|---|---|
|Leu|His|Arg|His|Ile|Phe|Trp|Glu|Pro|Asp|Ala|Ser|Lys|Leu|Asn|Glu|
| | | |420| | | |425| | | |430| | | |

Leu His Arg His Ile Phe Trp Glu Pro Asp Ala Ser Lys Leu Asn Glu
            420                 425             430

Asn Tyr Cys Arg Asn Pro Asp Asp Ala His Gly Pro Trp Cys Tyr
            435                 440             445

Thr Gly Asn Pro Leu Ile Pro Trp Asp Tyr Cys Pro Ile Ser Arg Cys
450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
                500                 505                 510

Ile Cys Gly Gly Ser Leu Ile Lys Glu Ser Trp Val Leu Thr Ala Arg
                515                 520                 525

Gln Cys Phe Pro Ser Arg Asp Leu Lys Asp Tyr Glu Ala Trp Leu Gly
            530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Ser Cys Ser
            595                 600                 605

Val Tyr Gly Trp Gly Tyr Thr Gly Leu Ile Asn Tyr Asp Gly Leu Leu
610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
            675                 680                 685

Gly Arg Gly Cys Ala Ile Pro Asn Arg Pro Gly Ile Phe Val Arg Val
690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 5
<211> LENGTH: 2187
<212> TYPE: DNA
<213> ORGANISM: Rattus norvegicus

<400> SEQUENCE: 5

```
atgatgtggg ggaccaaact tctgccggtc ctgttgctgc agcatgtcct gctgcacctc      60
ctcctgcttc ctgtcaccat ccctatgca gaaggacaga gaagagaag aaatactctt      120
catgaattca aaaagtcagc aaaaactact cttaccaagg aagacccatt agtgaagatt      180
aaaaccaaaa aagtgaactc tgcagatgag tgtgccaaca ggtgcatcag aaacaagggc      240
tttccattca cttgcaaggc ctttgttttt gataagtcga gaaaacgatg ctactggtat      300
cctttcaata gtatgtcaag tggagtgaaa aaagggtttg ccatgaatt tgacctctat      360
gaaaacaaag actatattag aaattgcatc attggtaaag gaggcagcta taaggggaca      420
```

```
gtatccatca ctaagagtgg catcaagtgc cagccttgga attccatgat cccccatgaa    480
cacagctttt tgccttcgag ctatcgcggt aaagacctac aggaaaacta ctgtcgaaat    540
cctcgagggg aagaagggg acctggtgt tcacaagca atccagaggt acgctacgaa       600
gtctgtgaca ttcctcagtg ttcagaagtt gaatgcatga cctgcaacgg tgaaagctac    660
agaggtccca tggatcacac agaatcagg aagacatgtc agcgctggga tcagcagaca     720
ccacaccggc acaaattctt gccggaaaga tatcccgaca agggctttga tgataattat    780
tgccgcaatc ccgatggcaa gccgaggcca tggtgctaca ctcttgaccc tgacacccct    840
tgggagtatt gtgcaattaa aatgtgcgct cacagtgctg tgaatgagac tgatgttccc    900
atggaaacaa ctgaatgtat aaaaggccaa ggagaaggtt acaggggaac caccaatacc    960
atttggaatg gaattccgtg tcagcgttgg gattcgcagt accccacaa gcatgacatc      1020 actcccgaga acttcaaatg caaggacctt agagaaaatt attgccgcaa tccggatggg    1080
gctgaatcac catggtgttt taccactgat ccaaacatcc gagttggtta ctgctctcaa    1140
attcccaaat gtgacgtgtc aagtggacaa gattgttatc gtggcaatgg gaaaaactac    1200
atgggcaact tatccaaaac aaggtctgga ctcacatgtt ccatgtggga caagaatatg    1260
gaggatttac accgtcatat cttctgggag ccagacgcta gcaagttgac taagaattac    1320
tgccggaacc ccgatgacga cgcccatgga ccttggtgct acacagggaa tcctctcgtt    1380
ccttgggatt attgccctat ttcccgttgt gaaggagata ctacacctac aattgtcaat    1440
ttggaccatc ctgtaatatc ctgtgccaaa acaaaacaac tgcgagttgt aaatggcatt    1500
ccaacacaaa caacagtagg gtggatggtt agtttgaaat acaggaataa acacatctgt    1560 ggggatcat tgataaagga aagttgggtt cttactgcaa ggcaatgttt tccagctaga      1620
aacaaagact tgaaagacta tgaagcttgg cttggaatcc atgatgtcca tgagagaggc    1680
gaggagaaac gcaaacagat cttaaacatt tcccagctag tctatggacc tgaaggctca    1740
gatttggttt tactgaagct tgctcgccct gcaatcctgg ataactttgt cagtacaatt    1800
gatttaccta gttatggctg tacaatccct gaaaagacta cttgcagtat ttacggctgg    1860
ggctacactg gattgatcaa cgcagatggt ttattacgag tagctcatct gtatattatg    1920
gggaatgaga aatgcagtca gcaccatcaa ggcaaggtga cttttgaatga gtctgaatta    1980 tgtgctgggg ctgaaaagat tggatcagga ccttgtgagg gagattatgg tggcccactc    2040
atttgtgaac aacacaaaat gagaatggtt cttggtgtca ttgttcctgg tcgtggatgt    2100
gccatcccaa atcgtcctgg tattttttgtt cgagtagcat attatgcaaa atggatacac    2160
aaagtaattt tgacatacaa gttgtaa                                        2187
```

<210> SEQ ID NO 6
<211> LENGTH: 728
<212> TYPE: PRT
<213> ORGANISM: Rattus norvegicus

<400> SEQUENCE: 6

Met Met Trp Gly Thr Lys Leu Leu Pro Val Leu Leu Gln His Val
1               5                   10                  15

Leu Leu His Leu Leu Leu Pro Val Thr Ile Pro Tyr Ala Glu Gly
            20                  25                  30

Gln Lys Lys Arg Arg Asn Thr Leu His Glu Phe Lys Lys Ser Ala Lys
        35                  40                  45

Thr Thr Leu Thr Lys Glu Asp Pro Leu Val Lys Ile Lys Thr Lys Lys
    50                  55                  60

```
Val Asn Ser Ala Asp Glu Cys Ala Asn Arg Cys Ile Arg Asn Lys Gly
 65                  70                  75                  80

Phe Pro Phe Thr Cys Lys Ala Phe Val Phe Asp Lys Ser Arg Lys Arg
                 85                  90                  95

Cys Tyr Trp Tyr Pro Phe Asn Ser Met Ser Ser Gly Val Lys Lys Gly
                100                 105                 110

Phe Gly His Glu Phe Asp Leu Tyr Glu Asn Lys Asp Tyr Ile Arg Asn
            115                 120                 125

Cys Ile Ile Gly Lys Gly Gly Ser Tyr Lys Gly Thr Val Ser Ile Thr
        130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Gly Pro Trp Cys Phe Thr
            180                 185                 190

Ser Asn Pro Glu Val Arg Tyr Glu Val Cys Asp Ile Pro Gln Cys Ser
        195                 200                 205

Glu Val Glu Cys Met Thr Cys Asn Gly Glu Ser Tyr Arg Gly Pro Met
210                 215                 220

Asp His Thr Glu Ser Gly Lys Thr Cys Gln Arg Trp Asp Gln Gln Thr
225                 230                 235                 240

Pro His Arg His Lys Phe Leu Pro Glu Arg Tyr Pro Asp Lys Gly Phe
                245                 250                 255

Asp Asp Asn Tyr Cys Arg Asn Pro Asp Gly Lys Pro Arg Pro Trp Cys
            260                 265                 270

Tyr Thr Leu Asp Pro Asp Thr Pro Trp Glu Tyr Cys Ala Ile Lys Met
        275                 280                 285

Cys Ala His Ser Ala Val Asn Glu Thr Asp Val Pro Met Glu Thr Thr
290                 295                 300

Glu Cys Ile Lys Gly Gln Gly Glu Gly Tyr Arg Gly Thr Thr Asn Thr
305                 310                 315                 320

Ile Trp Asn Gly Ile Pro Cys Gln Arg Trp Asp Ser Gln Tyr Pro His
                325                 330                 335

Lys His Asp Ile Thr Pro Glu Asn Phe Lys Cys Lys Asp Leu Arg Glu
            340                 345                 350

Asn Tyr Cys Arg Asn Pro Asp Gly Ala Glu Ser Pro Trp Cys Phe Thr
        355                 360                 365

Thr Asp Pro Asn Ile Arg Val Gly Tyr Cys Ser Gln Ile Pro Lys Cys
370                 375                 380

Asp Val Ser Ser Gly Gln Asp Cys Tyr Arg Gly Asn Gly Lys Asn Tyr
385                 390                 395                 400

Met Gly Asn Leu Ser Lys Thr Arg Ser Gly Leu Thr Cys Ser Met Trp
                405                 410                 415

Asp Lys Asn Met Glu Asp Leu His Arg His Ile Phe Trp Glu Pro Asp
            420                 425                 430

Ala Ser Lys Leu Thr Lys Asn Tyr Cys Arg Asn Pro Asp Asp Asp Ala
        435                 440                 445

His Gly Pro Trp Cys Tyr Thr Gly Asn Pro Leu Val Pro Trp Asp Tyr
450                 455                 460

Cys Pro Ile Ser Arg Cys Glu Gly Asp Thr Thr Pro Thr Ile Val Asn
465                 470                 475                 480

Leu Asp His Pro Val Ile Ser Cys Ala Lys Thr Lys Gln Leu Arg Val
```

```
                         485                 490                 495
Val Asn Gly Ile Pro Thr Gln Thr Thr Val Gly Trp Met Val Ser Leu
                500                 505                 510

Lys Tyr Arg Asn Lys His Ile Cys Gly Gly Ser Leu Ile Lys Glu Ser
                515                 520                 525

Trp Val Leu Thr Ala Arg Gln Cys Phe Pro Ala Arg Asn Lys Asp Leu
                530                 535                 540

Lys Asp Tyr Glu Ala Trp Leu Gly Ile His Asp Val His Glu Arg Gly
545                 550                 555                 560

Glu Glu Lys Arg Lys Gln Ile Leu Asn Ile Ser Gln Leu Val Tyr Gly
                565                 570                 575

Pro Glu Gly Ser Asp Leu Val Leu Leu Lys Leu Ala Arg Pro Ala Ile
                580                 585                 590

Leu Asp Asn Phe Val Ser Thr Ile Asp Leu Pro Ser Tyr Gly Cys Thr
                595                 600                 605

Ile Pro Glu Lys Thr Thr Cys Ser Ile Tyr Gly Trp Gly Tyr Thr Gly
                610                 615                 620

Leu Ile Asn Ala Asp Gly Leu Leu Arg Val Ala His Leu Tyr Ile Met
625                 630                 635                 640

Gly Asn Glu Lys Cys Ser Gln His His Gln Gly Lys Val Thr Leu Asn
                645                 650                 655

Glu Ser Glu Leu Cys Ala Gly Ala Glu Lys Ile Gly Ser Gly Pro Cys
                660                 665                 670

Glu Gly Asp Tyr Gly Gly Pro Leu Ile Cys Glu Gln His Lys Met Arg
                675                 680                 685

Met Val Leu Gly Val Ile Val Pro Gly Arg Gly Cys Ala Ile Pro Asn
                690                 695                 700

Arg Pro Gly Ile Phe Val Arg Val Ala Tyr Tyr Ala Lys Trp Ile His
705                 710                 715                 720

Lys Val Ile Leu Thr Tyr Lys Leu
                725

<210> SEQ ID NO 7
<211> LENGTH: 18
<212> TYPE: DNA
<213> ORGANISM: Artificial Sequence
<220> FEATURE:
<223> OTHER INFORMATION: Synthetic construct

<400> SEQUENCE: 7
ccgcccgagc cagagact                                                    18
```

AGENT FOR TREATING POLYGLUTAMINE AGGREGATION-CAUSED DISEASE OR SUPPRESSING ONSET THEREOF

This application is a U.S. national stage of International Application No. PCT/JP2007/057218 filed Mar. 30, 2007.

TECHNICAL FIELD

The present invention relates to an agent for treating a polyglutamine aggregation-caused disease or suppressing the onset thereof, in particular an agent comprising hepatocyte growth factor (hereinafter referred to as HGF) or DNA containing DNA encoding HGF as an active ingredient for treating a polyglutamine aggregation-caused disease or suppressing the onset thereof.

BACKGROUND ART

A polyglutamine aggregation-caused disease is an autosomal dominant progressive neurodegenerative disease. Abnormally expanded cytosine-adenine-guanine (CAG) repeats encoding polyglutamine are included in the gene responsible for polyglutamine aggregation-caused diseases. The translation of the gene responsible for polyglutamine aggregation-caused diseases having such abnormally expanded CAG repeats into the gene product, leads to the onset of polyglutamine aggregation-caused diseases. For example, with regard to Huntington's disease among polyglutamine aggregation-caused diseases, the huntingtin gene has been identified as a responsible gene and mapped in the short arm of chromosome 4 (see also The Huntington's Disease Collaborative Research Group, Cell, 1993; vol. 72: pp. 971-983). The huntingtin gene encodes the huntingtin protein of 3145 amino acid residues. This protein itself is expressed in various tissues and its full-length protein, which is nonpathogenic, is predominantly distributed in the cytoplasm. The CAG repeats are present in exon 1 of the huntingtin gene. When the gene is nonpathogenic, it has less than about 30 CAG repeats. The gene having about CAG repeats or more is pathogenic enough to induce Huntington's disease. From the gene with CAG repeats expanded to 30 or more, the huntingtin protein with longer glutamine repeats (polyglutamine) in the N-terminus, which is called mutant huntingtin, is produced. The mutant huntingtin with such a long stretch of polyglutamine is easy to aggregate. The long stretch of polyglutamine has been also reported to influence the interaction with other proteins and to promote the self-processing of the huntingtin protein therewith. Processed huntingtin protein is present abundantly in the nucleus, which results in toxicity to the cell and the onset of Huntington's disease. In general, Huntington's disease develops at the middle age and leads to death in 15 to 20 years after the onset. The symptom is characterized by distinctive uncoordinated muscle movement, cognitive deterioration and psychiatric symptoms, etc. The uncoordinated muscle movement is considered to result from a loss of coordination between voluntary movements and abnormal involuntary movements, including chorea and dystonia.

Meanwhile, HGF was first identified as a potent mitogen for mature hepatocytes and was determined by DNA cloning in 1989 (see also Nakamura, T., et al., Blochem. Biophys. Res. Commun., 1984; vol. 122: pp. 1450-1459 and Nakamura, T. et al., Nature, 1989; vol. 342: pp. 440-443). Kosai, K. et al. has reported that, via an anti-apoptotic effect, the administration of HGF prevents endotoxin-induced lethal hepatic failure accompanied by fulminant hepatic failure in mice (see also Hepatology 1999; vol. 30: pp. 151-159). Ueki, T. et al. has also reported that HGF gene therapy potentially improves the survival rate of rats with lethal liver cirrhosis (see also Nat. Med., 1999; vol. 5: pp. 226-230). Additionally, it has been demonstrated that HGF is also a novel neurotrophic factor through a large number of recent studies in the expression and functional analysis including knockout and knockin mice methods (see also Matsumoto, K. et al., Ciba Found. Symp., 1997; vol. 212, pp. 198-211; discussion 211-194 and Funakoshi, H. et al., Clin. Chim. Acta., 2003; vol. 327: pp. 1-23). Especially, HGF has been known to be one of the most potent survival factor for motoneurons in vitro, equivalent to glial cell line-derived neurotrophic factor (GDNF) according to Neuron, 1996; vol. 17: pp. 1157-1172. The accelerator for the GDNF production has been reported to be a therapeutic agent for amyotrophic lateral sclerosis (ALS), one of the neurodegenerative diseases according to JP-A No. 2002-47206. Further, HGF or a gene thereof has also been reported to slow the disease progression and increase the survival rate in ALS model transgenic mice, in which the expression of SOD1G93A, a human ALS-causing gene, is induced (see also JP-A No. 2002-87983 and Sun, W. et al., Brain Res. Mol. Brain. Res., 2002; vol. 103: pp. 36-48).

On the contrary, it has been known that GDNF gene delivery does not produce useful results in R6/2 Huntington's disease transgenic mice subjected to the lentivirus vector-mediated gene delivery of the GDNF gene (see also Popovic, N. et al., Exp. Neurol., 2005; vol. 193: pp. 65-74).

These facts as above indicate that polyglutamine aggregation-caused diseases such as Huntington's disease are completely different in etiology, pathology and pathogenesis mechanism, etc. from other neurodegenerative diseases including ALS, Alzheimer's disease and Parkinson's disease, and therefore all the neurodegenerative diseases cannot be treated alike.

The examples described in WO03-045439 show that the ethological and histological study was conducted as to the effects of the HGF gene on model rats of nigral dopamine neuron cell death. In the model rat, a drug administration has specifically destroyed nigral dopamine neurons in the mesencephalon, whose degeneration is typically observed in Parkinson's disease. The results of the study show that the preadministration of the HGF gene protected nigral dopamine neurons in the mesencephalon from neurotoxin 6-OHDA and inhibited the symptoms of model rats of nigral dopamine neuron cell death. Furthermore, based on these results, WO03-045439 discloses that the HGF gene is applicable to the treatment of neurodegenerative diseases such as not just Parkinson's disease, but also Alzheimer's disease, spinocerebellar ataxia, multiple sclerosis, striatonigral degeneration, spinal muscular atrophy, Huntington's disease, Shy-Drager syndrome, Charcot-Marie-Tooth disease, Friedreich's ataxia, myasthenia gravis, occlusive disease in the circle of Willis, amyloidosis, Pick's disease, subacute myelo-optico-neuropathy, dermatomyositis, multiple myositis, Creutzfeldt-Jakob disease, Behcet's disease, systemic lupus erythematosus, sarcoidosis, periarteritis nodosa, ossification of the posterior longitudinal ligament, multilevel spinal canal stenosis, mixed connective tissue disease, diabetic peripheral neuropathy and ischemic cerebrovascular disorders (cerebral infarction, cerebral hemorrhage, etc.). Huntington's disease is also listed as such a neurodegenerative disease.

However, while Parkinson's disease is a neurodegenerative disease caused by selective dropout of specific neurons, namely dopaminergic neurons in the substantia nigra, polyglutamine aggregation-caused disease develops due to the expression of the disease-causing gene product containing a long stretch of glutamine (polyglutamine) as mentioned above. The neurodegeneration or cell-death mechanism induced by 6-OHDA is totally different from that induced by the gene product responsible for polyglutamine aggregation-caused diseases. Therefore, even if HGF has the neuroprotective effects against 6-OHDA, it can be hardly expected to prevent the neurodegeneration or cell death in polyglutamine aggregation-caused diseases. From a clinical point of view, both of Parkinson's disease and a polyglutamine aggregation-caused disease are neurodegenerative diseases, but they have completely different pathologies and no correlation with each other. Additionally, their lesioned neurons are totally different. Accordingly, only the above-mentioned results of the study on Parkinson's disease model rats are not enough to say that HGF protein or DNA encoding the same is useful for the treatment of polyglutamine aggregation-caused diseases, and in fact, no reports have said so.

As mentioned above, therapeutic modalities of polyglutamine aggregation-caused diseases including Huntington's disease have not been established yet and in an extremely difficult situation.

DISCLOSURE OF THE INVENTION

Problems to be Solved by the Invention

The object of the present invention is to provide a useful medicament for treating a polyglutamine aggregation-caused disease or suppressing the onset thereof.

Means for Solving the Problems

The present inventors have carried out various investigations to achieve the above-mentioned object and found that excellent therapeutic effects on a polyglutamine aggregation-caused disease are exerted by HGF protein or a partial peptide of HGF protein that is substantially equivalent in activity to HGF protein (sometimes hereinafter referred to as HGF protein etc.), or DNA containing DNA encoding HGF protein etc. or DNA which encodes a protein that is substantially equivalent in activity to HGF protein and hybridizes with DNA comprising a complementary base sequence of the above-mentioned DNA under a stringent condition (sometimes hereinafter referred to as HGF gene). Through further investigations, the present invention has been completed.

First, the present inventors studied the involvement of HGF protein etc. or HGF gene in polyglutamine aggregation-caused diseases using R6/2 transgenic mice with pathogenic mutant huntingtin exon 1 containing long CAG repeats (mutant HD exon 1), as a mouse model of polyglutamine aggregation-caused disease (including Huntington's disease).

The present inventors delivered rat HGF gene into the striatum of the above-mentioned R6/2 transgenic mice by using a neurotrophic replication-incompetent herpes simplex virus type 1 (HSV-1) vector, to prepare the R6/2 transgenic mice expressing rat HGF protein in the striatum. By using the transgenic mouse, the practical effects of the HGF gene on a polyglutamine aggregation-caused disease were examined. As a result, the rat HGF gene-transferred mice surprisingly demonstrated the delayed onset of a clasping behavior, a phenomenon in which mice are unable to stretch their limbs, the prolonged lifespan and the improved motor dysfunctions. These findings are the first to show HGF protein expression exerts the therapeutic or onset-suppressing effects on a polyglutamine aggregation-caused disease including Huntington's disease.

Next, the present inventors studied the mechanism of therapeutic or onset-suppressing effects of HGF protein etc. or HGF gene on a polyglutamine aggregation-caused disease. As a result, they found that through at least two novel mechanisms of caspase-3 and/or caspase-1 activation-inhibiting action and neurogenesis action in the striatum, HGF protein or HGF gene brings useful effects on a polyglutamine aggregation-caused disease. HGF protein etc. or HGF gene inhibits striatal neurodegeneration or cell death through caspase-3 and/or caspase-1 activation-inhibiting action, so that it can inhibit striatal atrophy and ventricular dilatation as well. Namely, HGF protein or HGF gene improves motor dysfunction and extends a lifespan in a polyglutamine aggregation-caused disease through two actions of neurogenesis as well as inhibiting neurodegeneration or cell death.

Furthermore, the present inventors focused much attention on the fact that the long polyglutamine in the mutant huntingtin acquires neurotoxicity through fragmentation (processing) and examined the effects of HGF protein or HGF gene on the processing. As a result, they found that while R6/2 transgenic mice subjected to mutant HD exon 1 delivery showed the fragmentation of huntingtin protein, R6/2 transgenic mice treated with HGF gene delivery demonstrated the inhibition of the huntingtin protein fragmentation.

Such effects of HGF protein or HGF gene were first revealed by the present invention. Based on the findings, the present inventors have carried out further investigations and finally completed the present invention.

The present invention relates to:

1. an agent, which may be a composition or a preparation, for treating a polyglutamine aggregation-caused disease or suppressing an onset thereof, comprising, as an active ingredient,
   (1) (i) HGF protein, (ii) a partial peptide of HGF protein that is substantially equivalent in activity to HGF protein, or a salt of either of them, or
   (2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition;

2. the agent for treating a polyglutamine aggregation-caused disease or suppressing an onset thereof according to the above 1, wherein the active ingredient is (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition;

3. the agent for treating a polyglutamine aggregation-caused disease or suppressing an onset thereof according to the above 2, wherein the DNA encoding HGF protein is DNA containing (a) DNA comprising a base sequence represented by SEQ ID NO: 1, 2 or 5, or (b) DNA which encodes a protein that is substantially equivalent in activity to HGF protein and hybridizes with DNA comprising a complementary base sequence of the above-mentioned (a) under a stringent condition;

4. the agent for treating a polyglutamine aggregation-caused disease or suppressing an onset thereof according to the above 2 or 3, wherein the DNA is inserted into herpes simplex virus type 1 (HSV-1) vector, adenovirus vector or adeno-associated virus vector;

5. the agent for treating a polyglutamine aggregation-caused disease or suppressing an onset thereof according to the above 1, wherein the active ingredient is (i) HGF protein, (ii) a partial peptide of HGF protein that is substantially equivalent in activity to HGF protein, or a salt of either of them;

6. the agent for treating a polyglutamine aggregation-caused disease or suppressing an onset thereof according to the above 5, wherein the HGF protein has (a) a same amino acid sequence that is represented by SEQ ID NO: 3, 4 or 6, or (b) an amino acid sequence that is substantially equal to the above-mentioned amino acid sequence;

7. the agent for treating a polyglutamine aggregation-caused disease or suppressing an onset thereof according to any of the above 1 to 6, wherein the polyglutamine aggregation-caused disease is at least one disease selected from the group consisting of Huntington's disease, spinal and bulbar muscular atrophy, type 1, 2, 3, 6, 7 and 12 of spinocerebellar ataxia, dentatorubral-pallidoluysian atrophy and the like;

8. the agent for treating a polyglutamine aggregation-caused disease or suppressing an onset thereof according to any of the above 1 to 6, wherein the polyglutamine aggregation-caused disease is Huntington's disease;

9. the agent for treating a polyglutamine aggregation-caused disease or suppressing an onset thereof according to any of the above 1 to 8, wherein the agent is used for topical administration to an area affected by the polyglutamine aggregation-caused disease;

10. the agent for treating a polyglutamine aggregation-caused disease or suppressing an onset thereof according to the above 9, wherein the topical administration is intrathecal administration;

11. an agent for inhibiting ventricular dilatation, comprising, as an active ingredient,
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition;

12. an agent for inhibiting neurodegeneration or cell death dependent on a gene product responsible for a polyglutamine aggregation-caused disease, comprising, as an active ingredient,
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition;

13. an agent for inhibiting caspase-3 and/or caspase-1 activation in a neuron, comprising, as an active ingredient,
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition;

14. an agent for inhibiting a processing of a gene product responsible for a polyglutamine aggregation-caused disease, comprising, as an active ingredient,
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition;

15. the agent for treating a polyglutamine aggregation-caused disease or suppressing an onset thereof according to any of the above 1 to 10, wherein an effect on treating the polyglutamine aggregation-caused disease or suppressing the onset thereof results from inhibiting ventricular dilatation;

16. the agent for treating a polyglutamine aggregation-caused disease or suppressing an onset thereof according to the above 15, wherein the ventricular dilatation is caused by striatal neurodegeneration or cell death dependent on a gene product responsible for the polyglutamine aggregation-caused disease;

17. the agent for treating a polyglutamine aggregation-caused disease or suppressing an onset thereof according to the above 16, wherein the striatal neurodegeneration or cell death is caused by caspase-3 and/or caspase-1 activation;

18. the agent for treating a polyglutamine aggregation-caused disease or suppressing an onset thereof according to any of the above 1 to 10, wherein an effect on treating the polyglutamine aggregation-caused disease or suppressing the onset thereof results from neurogenesis;

19. the agent for treating a polyglutamine aggregation-caused disease or suppressing an onset thereof according to any of the above 1 to 10, wherein an effect on treating the polyglutamine aggregation-caused disease or suppressing the onset thereof results from inhibiting a processing of a gene product responsible for the polyglutamine aggregation-caused disease;

20. a use of
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition,
for a manufacture of an agent for treating a polyglutamine aggregation-caused disease or suppressing an onset thereof;

21. a method for treating a polyglutamine aggregation-caused disease or suppressing an onset thereof, comprising an administration to a mammal of
(1) (i) HGF protein, (ii) a partial peptide of HGF protein that is substantially equivalent in activity to HGF protein, or a salt of either of them, or (2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition; and 22. a use of
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition,
as an agent for treating a polyglutamine aggregation-caused disease or suppressing an onset thereof.

The present invention also relates to:
a method for inhibiting ventricular dilatation;
a method for inhibiting neurodegeneration or cell death dependent on the gene product responsible for a polyglutamine aggregation-caused disease;
a method for inhibiting caspase-3 and/or caspase-1 activation; or
a method for inhibiting the processing of the gene product responsible for a polyglutamine aggregation-caused disease; comprising
an administration to a mammal of
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition.

The present invention further relates to:
a use of
(1) (i) HGF protein, (it) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition,
for the manufacture of
a medicament for inhibiting ventricular dilatation;
a medicament for inhibiting neurodegeneration or cell death dependent on the gene product responsible for a polyglutamine aggregation-caused disease;
a medicament for inhibiting caspase-3 and/or caspase-1 activation; or
a medicament for inhibiting the processing of the gene product responsible for a polyglutamine aggregation-caused disease.

The present invention furthermore relates to:
a use of
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition,
as a medicament for inhibiting ventricular dilatation;
a medicament for inhibiting neurodegeneration or cell death dependent on the gene product responsible for a polyglutamine aggregation-caused disease;
a medicament for inhibiting caspase-3 and/or caspase-1 activation; or
a medicament for inhibiting the processing of the gene product responsible for a polyglutamine aggregation-caused disease.

EFFECT OF THE INVENTION

The therapeutic or onset-suppressing agent of the present invention exerts remarkably excellent effects on treating or suppressing the onset of polyglutamine aggregation-caused diseases such as Huntington's disease, spinal and bulbar muscular atrophy, type 1, 2, 3, 6, 7 or 12 of spinocerebellar ataxia or dentatorubral-pallidoluysian atrophy.

BEST MODE FOR CARRYING OUT THE INVENTION

Figure 1:
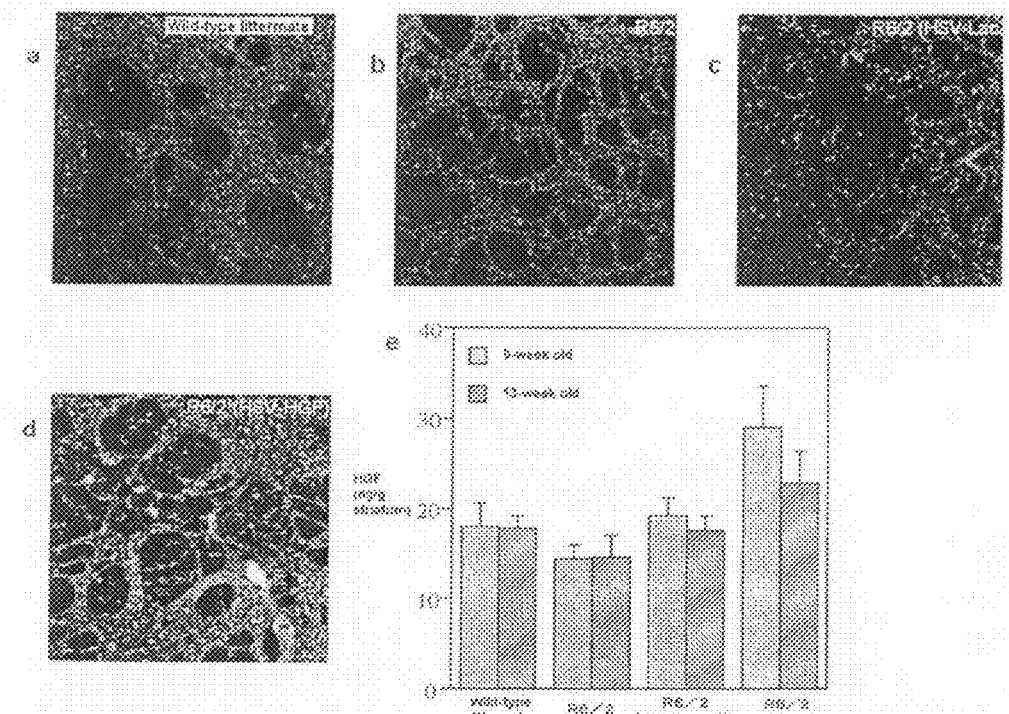
FIG. 1 shows the HGF expression in the striatum of HSV-HGF-transferred R6/2 mice. Each Panel shows the histology image of striatum of (a) wild-type littermate mice, (b) R6/2 mice, (c) R6/2(HSV-LacZ) mice and (d) R6/2(HSV-HGF) mice. Panel (e) shows the striatal HGF levels of mice in each group measured by ELISA.

As used herein, "DNA encoding HGF protein" refers to DNA capable of expressing HGF protein. Preferable examples of DNA containing the DNA encoding HGF protein include DNA encoding human HGF protein, for example described in Nature, vol. 342, 440 (1989); JP No. 2777678; Biochem. Biophys. Res. Commun., 1989, vol. 163, pp. 967-973; Proc. Natl. Acad. Sci. U.S.A., 1991, vol. 88(16), pp. 7001-7005, etc. and registered as Accession No. M60718, M73240, AC004960, AY246560, M29145, M73240 or the like in GenBank/EMBL/DDBJ. The DNA encoding HGF protein as used herein also includes DNA which encodes a protein that is substantially equivalent to HGF protein in activity such as mitogen activity, motogen activity and the like, and hybridizes with DNA comprising a complementary base sequence of the above-mentioned DNA under a stringent condition.

To be more specific, preferable examples of the DNA encoding HGF protein include DNA having a base sequence represented by SEQ ID NO: 1 or 2, or DNA which encodes a protein that is substantially equivalent to HGF protein in activity such as mitogen activity, motogen activity and the like and hybridizes under a stringent condition with DNA comprising a complementary base sequence of DNA having a base sequence represented by SEQ ID NO: 1 or 2. The base sequence represented by SEQ ID NO: 1 is equal to the region from the 73rd to the 2259th of the base sequence registered as Accession No. M60718, and is also equivalent to DNA encoding HGF protein comprising an amino sequence represented by SEQ ID NO: 3. The base sequence represented by SEQ ID NO: 2 is equal to the region from the 66th to the 2237th of the base sequence registered as Accession No. M73240, and is also equivalent to DNA encoding HGF protein comprising an amino sequence represented by SEQ ID NO: 4.

The "DNA which hybridizes under a stringent condition with DNA comprising a complementary base sequence of DNA having a base sequence represented by SEQ ID NO: 1 or 2" refers to DNA obtained by using a partial sequence of the above-mentioned DNA as a probe and carrying out hybridization such as colony hybridization, plaque hybridization, southern blot hybridization, etc. Specifically, DNA identified by the following procedures is included. A filter on which colony- or plaque-derived DNA has been immobilized is subjected to hybridization at about 65° C. in the presence of about 0.7 to 1.0 M sodium chloride, and then the filter is washed at about 65° C. in SSC solution at about 0.1- to 2-fold concentration (one fold concentration of SSC solution consisting of 150 mM sodium chloride and 15 mM sodium citrate). The stringent condition will be the same hereinafter.

To be more specific, the DNA which hybridizes under a stringent condition with DNA comprising a complementary base sequence of DNA having a base sequence represented by SEQ ID NO: 1 or 2 includes DNA having a base sequence about 80% or more, preferably about 90% or more and more preferably about 95% or more homologous to the counterpart represented by SEQ ID NO: 1 or 2. Hybridization can be performed according to known methods, for example the method described in Molecular Cloning, A laboratory Manual, Third Edition (J. Sambrook et al., Cold Spring Harbor Lab. Press, 2001; hereinafter abbreviated as Third Edition Molecular Cloning), etc. When a commercially available library is used, hybridization also can be performed in compliance with the method described in the attached instruction manual.

The DNA encoding HGF protein as used herein is not limited to the above-mentioned examples and includes any DNA as long as it encodes a protein that is substantially equivalent in activity to HGF protein after expression. For example, there can be preferably used DNA encoding a partial peptide of HGF protein that is substantially equivalent in activity to HGF protein.

Examples of the DNA encoding a partial peptide of HGF protein include any DNA which has a base sequence encoding the above-mentioned partial peptide and encodes a peptide that is substantially equivalent in activity to HGF protein. Specifically, examples of the DNA encoding a partial peptide as used herein include (a) DNA which has a partial base sequence of DNA having a base sequence represented by SEQ ID NO: 1 or 2, and encodes a peptide that is substantially equivalent in activity to HGF protein and (b) DNA which encodes a protein that is substantially equivalent in activity to HGF protein and hybridizes under a stringent condition with DNA comprising a complementary base sequence of DNA having a partial base sequence of DNA having a base sequence represented by SEQ ID NO: 1 or 2. To be more specific, such DNA preferably includes, for example, DNA having the region from the 94th to the 630th of human HGF base sequence represented by SEQ ID NO: 1 (DNA encoding a peptide from the N-terminal hairpin loop to the 1st kringle domain of HGF protein), and DNA having the region from the 94th to the 864th of human HGF base sequence represented by SEQ ID NO: 1 (DNA encoding a peptide from the N-terminal hairpin loop to the 2nd kringle domain of HGF protein).

DNA encoding HGF protein or DNA encoding a partial peptide of HGF protein that is substantially equivalent in activity to HGF protein can be easily obtained by, for example, a conventional hybridization and PCR method, etc. Specifically, the DNA can be obtained with reference to basic manuals, for example, the above-mentioned Third Edition Molecular Cloning and the like.

According to the present invention, DNA containing DNA encoding HGF protein or DNA encoding a partial peptide of HGF protein that is substantially equivalent in activity to HGF protein preferably includes genomic DNA, genomic DNA library, cell- or tissue-derived cDNA, cell- or tissue-derived cDNA library, synthetic DNA or the like. Examples of vectors used for cloning of genomic DNA fragments into the above-mentioned library include bacteriophages, plasmids, cosmids, phagemids or the like.

In the present invention, there also can be used RNA encoding HGF protein or RNA encoding a partial peptide of HGF protein that is substantially equivalent in activity to HGF protein, as long as HGF protein or the partial peptide can be expressed by reverse transcriptase. Examples of the RNA include RNA obtained by RT-PCR amplification of mRNA fraction harvested from cells or tissues, which is within the scope of the present invention. The RNA also can be obtained by known methods.

HGF protein as used herein is a known substance, and HGF protein can be prepared by any method for actual use as long as it is purified enough to be used as a medicament.

HGF protein can be obtained by culturing primary cultured cells or cell lines capable of producing HGF protein, followed by separation of the cells from culture supernatant etc. and purification. Alternatively, the protein can be obtained by genetic engineering methods, for example, by inserting the gene encoding HGF protein into an appropriate vector, transforming an appropriate host cell by transfection with the vector and isolating a desired recombinant HGF protein from culture supernatant of the transformant, etc. (see also JP-A No. 5-111382 and Biochem. Biophys. Res. Commun. 1989; vol. 163: p. 967, etc.). The above-mentioned host cell is not particularly limited and includes various host cells conventionally used in genetic engineering methods, for example, *Escherichia coli*, yeast, animal cells or the like. As long as the thus-obtained HGF protein is substantially equivalent in activity to native HGF protein, one or more ("more" means for example, 2 to 20 amino acids, preferably 2 to 10 amino acids and more preferably 2 to 5 amino acids; the same shall apply hereinafter) amino acids in the amino acid sequence may be substituted, deleted or added, and similarly, its sugar chain may be substituted, deleted or added. Such HGF protein can include 5-amino-acid-deleted-type HGF protein mentioned below. "One or more amino acids in the amino acid sequence may be substituted, deleted or added" means that a certain number (one or more) of the amino acids are substituted, deleted or added, etc. with the proviso that the number can be given by known technical methods such as a genetic engineering method and site specific mutagenesis or in a natural manner. "HGF protein in which a sugar chain is substituted, deleted or added" includes, for example, HGF protein in which a sugar chain in native HGF protein has been deleted by treatment with an enzyme or the like, HGF protein where the glycosylation site of the amino acid sequence has been mutated so as to prevent glycosylation or HGF protein where any other site of the amino acid sequence than the glycosylation site in native HGF protein has been mutated so as to be subjected to glycosylation. Specifically, there can be included, for example, HGF protein which is designed to prevent glycosylation by replacing Asn289, Asn397, Thr471, Asn561 and Asn648 with Gln289, Gln397, Gly471, Gln561 and Gln648 in human HGF protein registered as Accession No. NP_001010932 in the NCBI database (see also Fukuta, K. et al., Biochemical Journal, 2005; vol. 388: pp. 555-562).

Further, Examples of the HGF protein to be used in the present invention includes a protein having an amino acid sequence at least about 80% or more, preferably about 90% or more and more preferably about 95% or more homologous to the counterpart of HGF protein and being substantially equivalent in activity to HGF protein. "Homologous" in the above-mentioned amino acid sequence means the extent of correspondence of amino acid residues composing each amino sequence in comparison with the primary structure of each protein.

A preferred example of the HGF protein includes a protein of human origin represented by the amino acid sequence registered as Accession No. P14210 (SEQ ID NO: 3) or NP_001010932 (SEQ ID NO: 4) in the NCBI database or the like. The HGF protein having an amino acid sequence represented by SEQ ID NO: 4 is a 5-amino-acid-deleted type HGF protein, in which five amino acids from the 161st to the 165th in the amino acid sequence represented by SEQ ID NO: 3 are deleted. The protein having an amino acid sequence represented by SEQ ID NO: 3 or 4 is a native HGF protein of human origin with mitogen activity, motogen activity and the like as HGF.

The protein having an amino sequence substantially equal to the amino acid sequence represented by SEQ ID NO: 3 or 4 includes a protein having an amino acid sequence at least about 80% or more, preferably about 90% or more and more preferably about 95% or more homologous to the counterpart represented by SEQ ID NO: 3 or 4 and being substantially equivalent in activity to HGF protein. For example, preferred is a protein having an amino acid sequence where one or more amino acid residues are inserted or deleted, having an amino acid sequence where one or more amino acid residues are substituted with another (or more) amino acid residue(s), or having an amino acid sequence where one or more amino acid residues are modified in the amino acid sequence represented by SEQ ID NO: 3 or 4, and being substantially equivalent in activity to HGF protein. An amino acid to be inserted or substituted may be an unnatural amino acid other than 20 kinds of amino acids encoded by the gene. The unnatural amino acid may be any compound as long as it has an amino group and a carboxyl group, and for example, γ-aminobutyric acid etc. is included.

These proteins can be used alone or as a mixture of them. Examples of the protein having an amino acid sequence substantially equal to the amino acid sequence represented by SEQ ID NO: 3 or 4 include HGF of human origin registered as Accession No. BAA14348 or AAC71655, etc. in the NCBI database, but it is not limited thereto.

As HGF protein or DNA encoding the same to be used in the present invention, the above-mentioned protein or DNA of human origin is suitably used for human application, and in addition, HGF protein or DNA encoding the same derived from other mammals than human, such as monkey, cattle, horse, pig, sheep, dog, cat, rat, mouse, rabbit, hamster, guinea pig and chimpanzee, may be used. Such HGF includes, but is not limited to, HGF registered in the NCBI database or the like, for example, mouse HGF (for example, registered as Accession No. AAB31855, NP_034557, BAA01065, BAA01064 or the like), rat HGF (for example, registered as Accession No. NP_58713 (a protein having an amino acid sequence represented by SEQ ID No. 6) or the like), bovine HGF (for example, registered as Accession No. NP_001026921, XP874086, BAD02475 or the like), feline HGF (for example, registered as Accession No. NP_001009830, BAC10545, BAB21499 or the like), canine HGF (for example, registered as Accession No. NP_001002964, BAC57560 or the like), or chimpanzee HGF (for example, registered as Accession No. XP519174 or the like).

The HGF protein to be used in the present invention has any one of a carboxyl group (—COOH), a carboxylate (—COOM (M represents a metal)), an amide (—CONH$_2$) or an ester (—COOR) in the C-terminus. As used herein, R in the ester includes a C1-C6 alkyl group such as methyl, ethyl, n-propyl, isopropyl and n-butyl, a C3-C8 cycloalkyl group such as cyclopentyl and cyclohexyl, a C6-C12 aryl group such as phenyl and α-naphthyl, a C7-C14 aralkyl group such as a phenyl-(C1-C2 alkyl) group including benzyl and phenethyl and an α-naphthyl-(C1-C2 alkyl) group including α-naphthylmethyl, and further a C2-C6 alkanoylmethyl group such as acetyloxymethyl and pivaloyloxymethyl. When the HGF protein to be used in the present invention has a carboxyl group or a carboxylate in any other site than the C-terminus, the carboxyl group or carboxylate may be amidated or esterified and such HGF protein is included in the HGF protein of the present invention. In this case, the ester includes the above-mentioned examples of the ester in the C-terminus. Further, the HGF protein to be used in the present invention includes the above-mentioned protein having an amino group of the N-terminal methionine residue protected with a protecting group (for example, a C1-C6 acyl group such as a formyl group and a C2-C6 alkanoyl group such as acetyl, etc.), the above-mentioned protein having a glutamyl group pyroglutamated after being produced by cleaving the N-terminal side in a living body, the above-mentioned protein having a side chain reactive group of the amino acid within a molecule (for example, —OH, —SH, an amino group, an imidazolyl group, an indolyl group and a guanidino group, etc.) protected with an appropriate protecting group (for example, a C1-C6 acyl group such as a formyl group and a C2-C6 alkanoyl group such as acetyl, etc.) and a protein complex such as a glycoprotein, which is produced by glycosylating the above-mentioned protein.

The partial peptide of HGF protein as used herein that is substantially equivalent in activity to the HGF protein (sometimes hereinafter abbreviated as HGF partial peptide) may be any peptide as long as it is a partial peptide of the above-mentioned HGF protein and is substantially equivalent in activity to the HGF protein. According to the present invention, preferred is, for example, an HGF partial peptide having an amino acid sequence which constitutes the above-mentioned HGF protein and comprises at least about 20 amino acids or more, preferably about 50 amino acids or more, more preferably about 100 amino acids or more. Specifically, for example, included are a peptide having the amino acid sequence between the 32nd and the 210th from the N-terminus in human HGF amino acid sequence represented by SEQ ID NO: 3 (an amino acid sequence from the N-terminal hairpin loop to the 1st kringle domain of HGF protein), a peptide having the amino acid sequence between the 32nd and the 288th from the N-terminus in human HGF amino acid sequence represented by SEQ ID NO: 3 (an amino acid sequence from the N-terminal hairpin loop to the 2nd kringle domain of HGF protein), and the like.

The HGF partial peptide to be used in the present invention has any one of a carboxyl group (—COOH), a carboxylate (—COOM (M represents the same as defined above)), an amide (—CONH$_2$) or an ester (—COOR(R represents the same as defined above)) in the C-terminus. Further, like the above-mentioned HGF protein, the HGF partial peptide to be used in the present invention includes the above-mentioned peptide having an amino group of the N-terminal methionine residue protected with a protecting group, the above-mentioned peptide having a glutamyl group pyroglutamated after being produced by cleaving the N-terminal side in a living body, the above-mentioned peptide having a side chain functional group of the amino acid within a molecule protected with an appropriate protecting group and a protein complex such as a glycoprotein, which is produced by glycosylating the above-mentioned peptide.

A salt of the HGF protein or a partial peptide thereof includes a physiologically acceptable salt with an acid or a base, and inter alia, a physiologically acceptable salt with an acid is most preferable. Examples of such a salt include a salt with an inorganic acid (for example, hydrochloric acid, phosphoric acid, hydrobromic acid, sulfuric acid or the like) or a salt with an organic acid (for example, acetic acid, formic acid, propionic acid, fumaric acid, maleic acid, succinic acid, tartaric acid, citric acid, malic acid, oxalic acid, benzoic acid, methanesulfonic acid, benzenesulfonic acid or the like).

The HGF partial peptide or a salt thereof to be used in the present invention can be prepared by known peptide synthesis methods or by cleaving HGF protein with an appropriate peptidase. A peptide synthesis method may be, for example, a solid- or liquid-phase synthesis method. Namely, the desired peptide can be prepared by condensing a partial peptide or an amino acid which can constitute HGF protein and optionally has a protecting group with a remaining part optionally having a protecting group and then by removing the protecting group, if any, from the product. A known condensation or deprotection method includes methods described in, for example, M. Bodanszky and M. A. Ondetti, Peptide Synthesis, Interscience Publishers, New York (1966) and Schroeder and Luebke, The Peptide, Academic Press, New York (1965), etc. After the reaction, HGF partial peptide can be isolated and purified by a combination of customary purification methods such as solvent extraction, distillation, column chromatography, liquid chromatography, crystallization or recrystallization. When the thus-obtained partial peptide is in a free form, the partial peptide can be converted into an appropriate salt by a known method. Meanwhile, when the thus-obtained partial peptide is in the form of a salt, the peptide can be converted into a free form by a known method.

A "polyglutamine aggregation-caused disease" of the present invention is typically exemplified by an inherited neurodegenerative disease, in which the disease-causing gene having about 30 or more of cytosine-adenine-guanine (CAG indicates a codon for glutamine) repeats is transcribed and translated into the gene product having an abnormally expanded glutamine stretch (polyglutamine) and subsequently the abnormal accumulation or aggregation of the gene product in the neuron induces neurodegeneration or cell death and dysfunctions such as uncoordinated muscle movement (for example, chorea and dystonia, etc.), cognitive deterioration or psychiatric symptoms.

Specifically, examples of the polyglutamine aggregation-caused disease include Huntington's disease, spinal and bulbar muscular atrophy, type 1, 2, 3, 6, 7 or 12 of spinocerebellar ataxia or dentatorubral-pallidoluysian atrophy.

"Treating" as used herein refers to ameliorating the symptoms of a polyglutamine aggregation-caused disease or achieving full recovery from the polyglutamine aggregation-caused disease, and specifically includes, for example, inhibiting or delaying neurodegeneration or cell death in the polyglutamine aggregation-caused disease and thereby inhibiting or preventing the above-mentioned dysfunctions towards normalization. The "treating" also includes promoting neurogenesis in the area affected by neurodegeneration or cell death.

"Suppressing the onset" as used herein refers to inhibiting neurodegeneration or the progression thereof induced by the expression of the gene responsible for a polyglutamine aggregation-caused disease having about 30 CAG repeats or more and the production of the gene product thereof, and includes inhibiting or preventing the expression of the gene responsible for the polyglutamine aggregation-caused disease having about 30 CAG repeats or more and the production and accumulation of the gene product thereof.

The disease-causing gene includes, for example, the huntingtin gene. The huntingtin gene has CAG repeats in exon 1. When the huntingtin gene is nonpathogenic, it has less than about 30 CAG repeats in exon 1. When the huntingtin gene is pathogenic, it is exemplified by the gene having about 30 or more of the CAG repeats.

The method for suppressing the onset of a polyglutamine aggregation-caused disease includes, for example, (1) inhibiting or preventing the expression of the disease-causing gene having 30 CAG repeats or more, (2) inhibiting or preventing the production of the gene product from the disease-causing gene having 30 CAG repeats or more, (3) inhibiting or preventing the accumulation of the gene product from the disease-causing gene having 30 CAG repeats or more, (4) inhibiting the progression of neurodegeneration caused by the gene product responsible for a polyglutamine aggregation-caused disease or (5) inhibiting the processing of the gene product from the disease-causing gene having 30 CAG repeats or more. It is preferred that any one or more of the above-mentioned (1) to (5) are achieved.

In the present invention, the agent for treating a polyglutamine aggregation-caused disease or suppressing the onset thereof is applicable to human and is also applicable to other mammals than human, such as monkey, cattle, horse, pig, sheep, dog, cat, rat, mouse, rabbit, hamster, guinea pig and chimpanzee as well.

When the agent for treating a polyglutamine aggregation-caused disease or suppressing the onset thereof is administered to a patient, the dosage form, dosing method and dose, etc. may slightly vary with whether the active ingredient is HGF protein or DNA encoding the same.

For example, according to the present invention, a preparation comprising HGF protein as an active ingredient can be in any of various dosage forms such as a liquid or solid form. In general, it is preferred that HGF protein alone or in combination with a customary carrier is formulated into an injection, spray or sustained-release preparation (for example, a depot preparation), etc. The above-mentioned injection is either an aqueous or oily injection. The aqueous injection can be prepared by know methods. For example, to an aqueous solvent such as water for injection and purified water, is optionally added a pharmaceutically acceptable excipient, for example a tonicity agent (such as sodium chloride, potassium chloride, glycerin, mannitol, sorbitol, boric acid, borax, glucose, propylene glycol), a buffering agent (such as phosphate buffer solution, acetate buffer solution, borate buffer solution, carbonate buffer solution; citrate buffer solution, Tris-buffer solution, glutamic acid buffer solution, epsilon-aminocaproic acid buffer solution), a preservative (such as methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edetate, boric acid, borax), a thickener (such as hydroxyethyl cellulose, hydroxypropyl cellulose, polyvinyl alcohol, polyethylene glycol), a stabilizer (such as sodium bisulfite, sodium thiosulfate, sodium edetate, sodium citrate, ascorbic acid, dibutyl hydroxytoluene), a pH adjuster (such as hydrochloric acid, sodium hydroxide, phosphoric acid, acetic acid) or the like. Next, after HGF protein is dissolved in the resulting solution, the solution is sterile-filtered with a filter or the like. Finally, the filtered solution is filled into a sterile container. Additionally, an appropriate solubilizing agent, for example an alcohol (such as ethanol), polyalcohol (such as propylene glycol and polyethylene glycol), a nonionic surfactant (such as polysorbate 80 and polyoxyethylene (50) hydrogenated castor oil) or the like may be also incorporated. To prepare an oily injection, sesame oil, soy bean oil or the like may be used as an oily solvent and benzyl benzoate, benzyl alcohol or the like may be incorporated as a solubilizing agent. The prepared injection is usually filled into an appropriate ampule or vial, etc. The amount of the HGF protein in the injection can be adjusted to usually about 0.0002 to 0.2 w/v %, preferably about 0.001 to 0.1 w/v %. It is preferred that a liquid preparation such as an injection is frozen for preservation or stored after removing moisture by lyophilization or the like. The lyophilized preparation can be used by adding distilled water for injection or the like as needed and redissolving the preparation.

A spray also can be prepared by common methods in the formulation practice. To prepare a spray, any excipient may be incorporated into the spray as long as the excipient is usually used for an inhaled preparation. For example, in addition to a propellant, the above-mentioned solvent, preservative, stabilizer, tonicity agent or pH adjuster, etc. can be incorporated. Examples of the propellant include a liquefied gas propellant or a compressed gas. Examples of the liquefied gas propellant include a fluorohydrocarbon such as a substitute for chlorofluorocarbons (e.g. HCFC22, HCFC-123, HCFC-134a, HCFC142 or the like), liquefied petroleum, dimethylether or the like. Examples of the compressed gas include a soluble gas such as carbon dioxide gas and nitrous oxide gas or an insoluble gas such as nitrogen gas.

The HGF protein to be used in the present invention together with a biodegradable polymer can be prepared in the form of a sustained-release preparation, for example, a depot preparation. Especially, a depot preparation of HGF protein can be expected to reduce the dose frequency, prolong the effect and reduce the side effect, etc. The sustained-release preparation can be prepared by known methods. The biodegradable polymer to be used in the sustained-release preparation can be appropriately selected from known biodegradable polymers, for example, a polysaccharide such as starch, dextran or chitosan; a protein such as collagen or gelatin; a polyamino acid such as polyglutamic acid, polylysine, polyleucine, polyalanine or polymethionine; a polyester such as polylactic acid, polyglycolic acid, lactic acid-glycolic acid copolymer, polycaprolactone, poly-β-hydroxybutyric acid, polymaleic acid, polyanhydride or fumaric acid-polyethylene glycol-vinylpyrrolidone copolymer; a polyortho ester or a polyalkyl cyanoacrylate such as polymethyl-α-cyanoacrylate; or a polycarbonate such as polyethylene carbonate or polypropylene carbonate. Preferred is a polyester and more preferred is polylactic acid or lactic acid-glycolic acid copolymer. When lactic acid-glycolic acid copolymer is used as a biodegradable polymer, the proportion based on the mole percentage (lactic acid/glycolic acid) depends on the duration of sustained release. For example, when the duration of sustained release is from about 2 weeks to 3 months, preferably from about 2 weeks to 1 month, the preferable proportion is from about 100/0 to 50/50. In general, the weight-average molecular weight of the polylactic acid or lactic acid-glycolic acid copolymer is preferably from about 5,000 to 20,000. The polylactic acid or lactic acid-glycolic acid copolymer can be prepared by known synthesis methods, for example the method disclosed by JP-A No. 61-28521. The proportion of HGF protein to the biodegradable polymer is not particularly limited, but a preferable proportion is from about 0.01 to 30 w/w % of HGF protein relative to the biodegradable polymer.

A preferable dosing method is direct injecting (an intrathecal administration, an administration into the spinal parenchyma, a continuous intrathecal administration with a sustained-release pump, or the like) or spraying an injection or a spray to the area affected by a polyglutamine aggregation-caused disease, or embedding a sustained-release preparation (a depot preparation) into the area near to the tissue affected by a polyglutamine aggregation-caused disease. Further, the dose is appropriately selected in response to the dosage form, disease progression, age or the like, and a single dose is usually 1 µg to 500 mg, preferably 10 µg to 50 mg, more preferably 1 to 25 mg. In addition, the dose frequency is also appropriately selected in response to the dosage form, disease progression, age or the like, and for example, a single dosing or a continuous dosing at a certain interval can be selected.

The continuous dosing may be performed between once daily and once several months. For example, the administration with the sustained-release preparation (a depot preparation) or the continuous intrathecal administration with a sustained-release pump may be performed once several months.

Meanwhile, it is preferred that the HGF gene is delivered to a patient in compliance with conventional methods, for example, the method described in "Idenshi Chiryo No Kiso-gijyutsu (Basic Technique for Gene Therapy)," a separate volume of Experimental Medicine, Yodosha Co., Ltd., 1996; "Idenshi Dounyu & Hatsugen Kaiseki Jikken-hou (Experimental Method for Gene Delivery and Expression Analysis)," a separate volume of Experimental Medicine, Yodosha Co., Ltd., 1997; and "Idenshi Chiryo Kaihatsu Kenkyu Handbook (Handbook for Research & Development in Gene Therapy)," edited by the Japan Society of Gene Therapy, NTS Inc., 1999; etc.

Specifically, examples of the method for delivering the HGF gene include a topical injection of a recombinant expression vector, etc. inserted with the HGF gene into the tissue affected by a polyglutamine aggregation-caused disease (for example, spinal nerve, brain or the like), or a transplantation of the transformed cell, which is prepared by taking a cell out from the disease-affected tissue or spinal cord, etc. of the patient and then transfecting the cell with a recombinant expression vector inserted with the HGF gene, into the disease-affected area or spinal cord of the patient.

Examples of the expression vector include, but are not limited to, a naked plasmid or a DNA or RNA virus such as a detoxified retrovirus, adenovirus, adeno-associated virus, herpes virus (herpes simplex virus type 1, etc.), vaccinia virus, poxvirus, poliovirus, sindbisvirus, sendai virus, SV40 or human immunodeficiency virus (HIV). DNA encoding HGF protein can be delivered into the cell by inserting the desired gene into the above-mentioned vector and then infecting the cell with the recombinant virus. Inter alia, most preferred is herpes simplex virus type 1 (HSV-1) vector, adenovirus vector, adeno-associated virus (AAV) vector or the like.

The HSV-1 vector is neurotrophic. The HSV-1 vector preferably has a 152-kb large genome inserted with a multigene (30 kb or less) and the potential of establishing a latent infection in the neuron over a lifetime. A specific HSV-1 vector includes a replication-incompetent HSV-1 (HSV1764/4-/pR19) vector severely impaired by the deletion of the three respective genes encoding ICR4, ICP34.5 and VP16 (vmw65), all of which are essential for viral replication (see also Coffin, R. S., et al., J. Gen. Virol. 1998, vol. 79, pp. 3019-3026; Palmer, J. A., et al., J. Virol., 2000, vol. 74, pp. 5604-5618; Lilley, C. E., et al., J. Virol., 2001, vol. 75, pp. 4343-4356; etc.). The AAV vector, which is a non-pathogenic virus, is highly safe and efficient in gene delivery into a nondividing cell such as a neuron. Examples of the AAV vector include AAV-2, AAV-4 and AAV-5. Such an HSV-1 or AAV vector is capable of expressing the target gene in the neuron etc. for a prolonged period of time. Since it is a long time before the pathology of the polyglutamine aggregation-caused disease is fully developed, the HSV-1 or AAV vector capable of a prolonged expression is most preferable as a vector to be used in the present invention.

For the evaluation of HGF on a polyglutamine aggregation-caused disease, the HGF gene is transfected into the area affected by a polyglutamine aggregation-caused disease such as striatum and medullary cavity using, for example, an HSV-1 or AAV vector.

The dosage form can be selected from various known forms (for example, an injection, spray, sustained-release preparation (depot preparation) or microcapsule etc.) in response to the above-mentioned respective dosing methods. The injection, spray and sustained-release preparation (depot preparation) can be prepared in the same manner as described in the case of HGF protein. A microcapsule can be prepared as a fine particle with a diameter of about 1 to 500 μm, preferably about 100 to 400 μm, by coating a core substance, for example a host cell etc. transfected with the HGF gene-containing expression plasmid, with a coating material in accordance with known methods (for example, coacervation method, interfacial polycondensation, a method using a double nozzle or the like). Examples of the coating material include a membranous polymer such as carboxymethyl cellulose, cellulose acetate phthalate, ethyl cellulose, alginic acid or a salt thereof, gelatin, gelatin-gum arabic, nitrocellulose, polyvinyl alcohol or hydroxypropyl cellulose, polylactic acid, polyglycolic acid, lactic acid-glycolic acid copolymer, chitosan-alginate, cellulose sulfate-poly(dimethyldiallyl)ammonium chloride, methacrylate-methyl methacrylate, chitosan-carboxymethyl cellulose, alginate-polylysine-alginate.

The amount of DNA in the dosage form and the dose are appropriately adjusted depending on the type of disease intended to be treated, the age and body weight of the patient and the like. The dose can vary according to the kind of the vector for HGF gene transfer, and it is usually $1 \times 10^6$ pfu to $1 \times 10^{12}$ pfu, preferably $1 \times 10^7$ pfu to $2 \times 10^{11}$ pfu, more preferably $1.5 \times 10^7$ pfu to $1.5 \times 10^{11}$ pfu in terms of an amount of a vector for HGF gene transfer between once several days to once several months.

The agent of the present invention can be used for treating or suppressing the onset of polyglutamine aggregation-caused diseases such as Huntington's disease, spinal and bulbar muscular atrophy, type 1, 2, 3, 6, 7 or 12 of spinocerebellar ataxia or dentatorubral-pallidoluysian atrophy, preferably Huntington's disease.

The therapeutic or onset-suppressing effects on a polyglutamine aggregation-caused disease can be determined by known methods (for example, a clasping test (cf. Nat. Med, vol. 10, pp. 148-154, Epub. 2004, Jan. 2018); a rotarod test (cf. J. Neurosci, 2000, vol. 20, pp. 4389-4397); a footprint test (cf. J. Neurosci, 1999, vol. 19, pp. 3248-3257); or the like) or the quasi methods, for example, the method described in the following test examples, etc.

According to the present invention, HGF protein or a partial peptide of HGF protein that is substantially equivalent in activity to HGF protein (HGF protein etc.), or DNA containing DNA encoding HGF protein, DNA encoding a partial peptide of HGF protein that is substantially equivalent in activity to HGF protein or DNA which encodes a protein that is substantially equivalent in activity to HGF protein and hybridizes with DNA comprising a complementary base sequence of either of the above-mentioned DNAs under astringent condition (HGF gene) can be used for inhibiting ventricular dilatation, inhibiting neurodegeneration or cell death dependent on the gene product responsible for a polyglutamine aggregation-caused disease, inhibiting caspase-3 and/or caspase-1 activation in the neuron, or promoting neurogenesis.

The ventricular dilatation can be induced by brain atrophy, especially striatal atrophy (for example, striatal atrophy resulting from striatal cell death). The HGF protein etc. or HGF gene of the present invention can inhibit the symptoms caused by ventricular dilatation such as motor dysfunction including extremity impairment, for example dysbasia etc., speech disorder, memory impairment or psychiatric symptoms.

The neurodegeneration or cell death dependent on the gene product responsible for a polyglutamine aggregation-caused disease can be induced by expression and accumulation of the gene product responsible for a polyglutamine aggregation-caused disease in the nervous tissues such as striatum. The HGF protein etc. or HGF gene of the present invention can inhibit the neurodegeneration or cell death dependent on the gene product responsible for a polyglutamine aggregation-caused disease, especially in the striatum. The cell death as used herein includes apoptosis and necrosis. Therefore, "inhibiting cell death" refers to inhibiting cell death simply and it includes the inhibition of apoptosis or necrosis, or the inhibition of both apoptosis and necrosis.

The HGF protein etc. or HGF gene of the present invention can inhibit the activation of a protease involved in the induction of the above-mentioned cell death and, for example it can inhibit the activation of a caspase, specifically caspase-1 or caspase-3. In human, there are about 10 to 20 kinds of caspases, and the activation of a caspase triggers that of another caspase, which is so called as a cascade reaction, finally inducing cell death. Among these caspases, caspase-3 has been known as an enzyme to carry out the cell-death program at the final stage of the caspase activation. Additionally, caspase-3 has been reported to be activated in Huntington's disease (see also Zhang, Y. et al., J. Neurochem., 2003, vol. 87, pp. 1184-1192). Caspase-3 is a protease to carry out the cell death program by degrading various intracellular proteins and it can be activated upon the induction of neurodegeneration or cell death in the neuron. "Inhibiting caspase-3 or caspase-1 activation" refers to inhibiting the activation of the above-mentioned caspase-3 or caspase-1. The effect of inhibition on caspase-3 or caspase-1 activation can be measured by known methods or the quasi methods (for example, Trends Biochem. Sci., 1997, vol. 22, pp. 388-393; Biochem. J., 1997, vol. 326, pp. 1-16; Anal. Biochem., 1997, vol. 251, pp. 98-102; or the like), or for example, the method described in the following test examples, etc.

The HGF protein etc. or HGF gene of the present invention relates to neurogenesis. The neurogenesis includes the proliferation of neuroblasts and neural stem cells, etc. that can be differentiated into neurons. The birth of a neuron requires cell division. During cell division, DNA is replicated so as to copy the genetic information. A marker for DNA replication includes, for example, bromodeoxyuridine (BrdU). For example, when BrdU is injected into the body, a new cell to be born takes the BrdU into the cell and thereby the degree of neurogenesis can be assessed by the BrdU as an indicator. Accordingly, the effect on neurogenesis can be determined by a method using BrdU uptake in brain neurons as an indicator or the method described in the following test examples, etc.

The HGF protein etc. or HGF gene of the present invention relates to the processing of the gene product responsible for a polyglutamine aggregation-caused disease. "Processing" refers to a process in which the transcription product is converted into a mature protein having an inherent localization and function while being subjected to partial degradation etc. by an intracellular protease and the like during the expression of the gene responsible for a polyglutamine aggregation-caused disease. The processing as used herein includes a fragmentation of the disease-causing gene product. A common characteristic of a polyglutamine aggregation-caused disease is an expanded polyglutamine stretch (30 glutamines or more) present in the gene responsible for any polyglutamine aggregation-caused disease. The expression of neurotoxicity in a polyglutamine aggregation-caused disease includes a fragmentation of the gene product from the disease-causing gene having 30 CAG repeats or more. For example, during the expression of the gene responsible for Huntington's disease (huntingtin gene) with CAG repeats expanded to 30 or more, the disease-causing gene product (mutant huntingtin) is fragmented through processing. The fragmented mutant huntingtin is considered to be pathogenic and neurotoxic. Against the backdrop of these findings, it can be assessed whether HGF gene inhibits the processing by measuring the inhibition rate of processing-mediated fragmentation of huntingtin protein. The effect of inhibition on the processing can be determined by, for example the method described in the following test examples, etc.

The present invention provides a use of
(1) (i) HGF protein, (ii) a partial peptide of HGF protein that is substantially equivalent in activity to HGF protein, or a salt of either of them, or
(2) DNA containing (i) DNA encoding HGF protein, (ii) DNA encoding a partial peptide of HGF protein that is substantially equivalent in activity to HGF protein or (iii) DNA which encodes a protein or a peptide that is substantially equivalent in activity to HGF protein and hybridizes with DNA comprising a complementary base sequence of either of the above-mentioned DNAs under a stringent condition,
as an agent for treating a polyglutamine aggregation-caused disease or suppressing the onset thereof. Further, the present invention also provides a use of the above-mentioned ingredient (1) or (2) for the manufacture of an agent for treating a polyglutamine aggregation-caused disease or suppressing the onset thereof.

According to the present invention, the method for treating a polyglutamine aggregation-caused disease or suppressing the onset thereof comprises an administration of the above-mentioned ingredient (1) or (2) to a mammal.

The present invention also provides a use of the above-mentioned ingredient (1) or (2) as an agent for inhibiting ventricular dilatation, and further for the manufacture of an agent for inhibiting ventricular dilatation.

According to the present invention, the method for inhibiting ventricular dilatation comprises an administration of the above-mentioned ingredient (1) or (2) to a mammal.

The present invention also provides a use of the above-mentioned ingredient (1) or (2) as an agent for inhibiting neurodegeneration or cell death dependent on the gene product responsible for a polyglutamine aggregation-caused disease, and further for the manufacture of an agent for inhibiting neurodegeneration or cell death dependent on the gene product responsible for a polyglutamine aggregation-caused disease.

According to the present invention, the method for inhibiting neurodegeneration or cell death dependent on the gene product responsible for a polyglutamine aggregation-caused disease comprises an administration of the above-mentioned ingredient (1) or (2) to a mammal.

The present invention also provides a use of the above-mentioned ingredient (1) or (2) as an agent for inhibiting caspase-3 and/or caspase-1 activation in the neuron, and further for the manufacture of an agent for inhibiting caspase-3 and/or caspase-1 activation in the neuron.

According to the present invention, the method for inhibiting caspase-3 and/or caspase-1 activation in the neuron comprises an administration of the above-mentioned ingredient (1) or (2) to a mammal.

The present invention also provides a use of the above-mentioned ingredient (1) or (2) as an agent for inhibiting the processing of the gene product responsible for a polyglutamine aggregation-caused disease, and further for the manufacture of an agent for inhibiting the processing of the gene product responsible for a polyglutamine aggregation-caused disease.

According to the present invention, the method for inhibiting the processing of the gene product responsible for a polyglutamine aggregation-caused disease comprises an administration of the above-mentioned ingredient (1) or (2) to a mammal.

The use of the medicament and method of the present invention is suitable for patients with a polyglutamine aggregation-caused disease such as Huntington's disease, spinal and bulbar muscular atrophy, type 1, 2, 3, 6, 7 or 12 of spinocerebellar ataxia or dentatorubral-pallidoluysian atrophy, preferably Huntington's disease.

EXAMPLE

The present invention will hereinafter be described with reference to the test examples, but it is not limited thereto.

Test Example 1

Effect of HGF on Huntington's Disease Transgenic Mice
1. Experimental Animals

Female B6CBAF1/J mice transplanted with ovaries from female B6CBA-TgN (mutant HD exon 1) 62 Gpb/J mice (see also Mangiarini, L. et al., Cell, 1996, vol. 87, pp. 493-506) were supplied by Jackson Laboratory (Bar Harbor, Me.), maintained and mated with male B6CBAF1/J mice.

The genetic patterns of the first filial generation mice were determined by PCR analysis of genomic DNA extracted from the tail tissue, and the mice having TgN62 Gpb gene were defined as R6/2 Huntington's disease model transgenic mice (hereinafter abbreviated as R6/2 mice). The littermate mice of the above-mentioned R6/2 mice having no TgN (mutant HD exon 1) 62 Gpb gene were defined as wild-type littermate mice for experimental use.

All the experiments were conducted in accordance with the guideline of the Animal Experiment Ethics Committee of Osaka University. All efforts were made to minimize animal suffering and the number of animals for use.
2. Construction, Preparation and Purification of the Vector pR19ratHGFKT3WPRE was prepared by substituting GFP (green fluorescent protein) gene of pR19GFPWPRE (see also Lilley, C. E. et al., J. Virol., 2001, vol. 75, pp. 4343-4356) with cDNA comprising a full-length DNA encoding rat HGF (rat HGF; SEQ ID NO: 5) tagged with KT3 epitope (3'-CCGCCCGAGCCAGAGACT-5'; SEQ ID NO: 7) (see also Sun, W. et al., J. Neurosci., 2002, vol. 22, pp. 6537-6548). The sequence of this vector (pR19ratHGFKT3WPRE) was confirmed by sequence analysis using ABI 310 capillary sequencer. Next, homologous recombination was performed by co-transfecting plasmid pR19ratHGFKT3WPRE and HSV1764/-4/pR19LacZ viral DNA into M49 cell. A white plaque was selected and then purified three times, and lastly a replication-incompetent virus was propagated by the method of Palmer, J. A. et al. (see also J. Virol., 2000, vol. 74, pp. 5604-5618). The expression of rat HGF was confirmed by immunostaining. The expression was also confirmed by western blot method and rat HGF Enzyme-Linked Immunosorbent Assay (ELISA). For use in the main test, HSV1764/-4/pR19HGF viral vector (HGF expression vector; hereinafter abbreviated as HSV-HGF) with a titer of $1\times10^9$ to $2\times10^9$ pfu (plaque forming unit)/mL and HSV1764/-4/pR19LacZ viral vector (HGF non-expression vector; hereinafter abbreviated as HSV-LacZ) with a titer of $1\times10^9$ to $1.5\times10^9$ pfu/mL were prepared.

3. Delivery of HSV into the Brain (In Vivo)

Four-week old R6/2 mice were deeply anesthetized by intravenous injection of 50 mg/kg pentobarbital. Each of the mice was placed into a Kopf stereotaxic instrument for brain operations and immobilized for injection into the striatum (−0.4 mm, ±1.8 mm and −3.5 mm in anterior-posterior, lateral and superior-inferior directions, respectively). The mice were injected with 5 μl of HSV-LacZ ($5 \times 10^6$ pfu) or HSV-HGF ($3 \times 10^5$ pfu). The injection into the mouse striatum was performed using a 10 μl Hamilton syringe at the speed of 0.3 μl/min. Hereinafter, the mice injected with HSV-LacZ and HSV-HGF are called R6/2 (HSV-LacZ) mice and R6/2 (HSV-HGF) mice, respectively.

4. Histological and Immunohistochemical Analysis

The mice were deeply anesthetized and perfused transcardially with ice-cold phosphate-buffered saline (PBS) followed by PBS containing 4% paraformaldehyde for fixation. The brain was cryoprotected stepwise with 10% and 20% sucrose, and then frozen. The frozen brain was serially sectioned at a thickness of 20 μm. The resulting cryosections were stained with Cresyl Violet, a dye used for staining for Nissl substance.

Immunohistochemical staining was performed by washing cryosections with PBS, soaking them into PBS supplemented with 10% goat or donkey serum for 1 hour and then incubating them in the presence of the antibody at 4° C. overnight.

The following antibodies were used.

(1) NeuN Antibody

Mouse monoclonal antibody (manufactured by Chemicon International; Cat No. MAB377) was diluted 500-fold for use.

(2) c-Met Antibody

Rabbit polyclonal antibody SP260 (manufactured by Santa Cruz Biotechnology; Cat No. sc-162) was diluted 50-fold for use.

(3) phosphorylated c-Met Antibody

Rabbit polyclonal antibody (manufactured by Biosource; Cat No. 44-888G) was diluted 100-fold for use.

(4) anti-Active Caspase-3 Antibody

Rabbit polyclonal antibody (manufactured by Promega; Cat No. G748) was diluted 125-fold for use.

5. Enzyme-Linked Immunosorbent Assay (ELISA)

HGF level in the tissue was determined using anti-HGF polyclonal antibody (manufactured by Tokushu Meneki) in the same manner as described in Sun, W. et al., Brain Res. Mol. Brain. Res., 2002, vol. 103, pp. 36-48.

6. Western Blot

The homogenate of the mouse striatum was prepared using 50 mM Tris-HCl (pH7.4), 150 mM NaCl, 1% (W/V) TritonX-100, 1 mM PMSF (Phenylmethanesulfonyl fluoride; manufactured by Wako Pure Chemical Industries, Ltd.), 2 μg/mL antipain (manufactured by Peptide Institute, Inc.), 2 μg/mL leupeptin (manufactured by Peptide Institute, Inc.) and 2 μg/mL pepstatin (manufactured by Peptide Institute, Inc.). The same amount of the protein (120 μg per lane) was subjected to SDS-polyacrylamidegel-electrophoresis (SDS-PAGE) using a 15% polyacrylamidegel. After the separation by SDS-PAGE, the protein was electrotransferred to polyvinylidene difluoride membrane (PVDF; manufactured by BIO-RAD). After the protein-transferred PVDF membrane was blocked with 10 mass % fat-free milk at room temperature for 2 hours, the membrane was blotted with anti-caspase-3 antibody (rabbit polyclonal antibody; Cat No. C9598, manufactured by Sigma) or anti-caspase-1 (p20) antibody (rabbit polyclonal antibody; Cat No. sc-1218-R, manufactured by Santa Cruz Biotechnology). Subsequently, the membrane blotted with the anti-caspase-3 or anti-caspase-1 antibody was incubated with a secondary antibody (manufactured by DakoCytomation) conjugated to horseradish peroxidase (HRP) and then developed with ECL reagents (Cat No. RPN2106, manufactured by Amersham Biosciences) in accordance with the product manual.

The band intensity was analyzed by NIH (National Institutes of Health) imaging software developed by Wayre Rasband.

7. Statistical Analysis

Data are represented as means±standard deviation (SD) and the statistical significance was evaluated by ANOVA with Fisher's protected least-significant difference (PLSD) test.

The data of each group were analyzed with Statview 5.0 (manufactured by SAS Institute, Inc.), and differences at the $P<0.05$ level were taken as statistically significant.

8. HGF Expression Induced by HSV Delivery

In vivo HGF expression was immunohistochemically examined. As shown in FIG. 1 a-d, at 9 weeks of age (i.e., 5-week post-infection with HSV-HGF or HSV-LacZ), HGF immunoactivity was increased in the striatum of R6/2(HSV-HGF) mice compared with R6/2 mice or R6/2(HSV-LacZ) mice.

As measured by ELISA, HGF protein levels in the striatum are shown as follows. In wild-type littermate mice at the 3rd day post-injection of HSV-HGF, the striatal HGF protein level was increased to 47.07±5.81 ng/g by about 3-fold compared with R6/2 mice. The striatal HGF protein level was significantly increased in 9-week-old R6/2(HSV-HGF) mice compared with age-matched R6/2 or R6/2(HSV-LacZ) mice. Further, as shown in FIG. 1e, the striatal HGF protein level was also significantly increased in 13-week-old R6/2(HSV-HGF) mice compared with age-matched R6/2 or R6/2 (HSV-LacZ) mice, but the increases were more modest at 13 weeks of age than at 9 weeks of age.

9. Change in Body Weight

Figure 2:
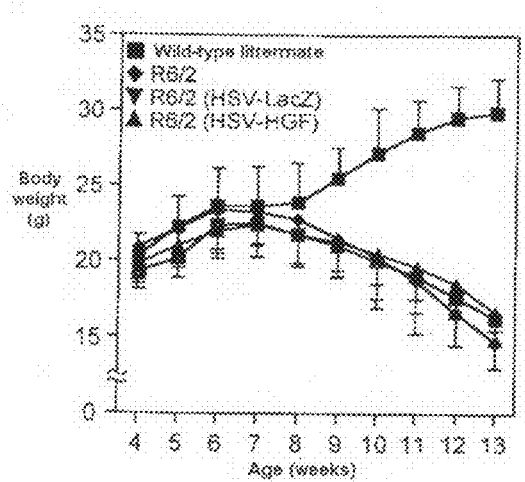
FIG. 2 shows the time-course in body weight of R6/2 mice in which HSV-HGF or HSV-LacZ was transferred into the striatum.

The mouse body weight was periodically measured after the viral infection. As shown in FIG. 2, the body weight was significantly decreased in 9-week-old R6/2 or R6/2(HSV-LacZ) mice compared with age-matched wild-type littermate mice. No differences were found in body weight between R6/2(HSV-HGF) and R6/2 mice.

10. Survival Curve

The survival curve for R6/2 mice and R6/2(HSV-HGF) mice was calculated by the Kaplan-Meier method and the log-rank test was conducted using Statview 5.0 (manufactured by SAS Institute, Inc).

Figure 3:
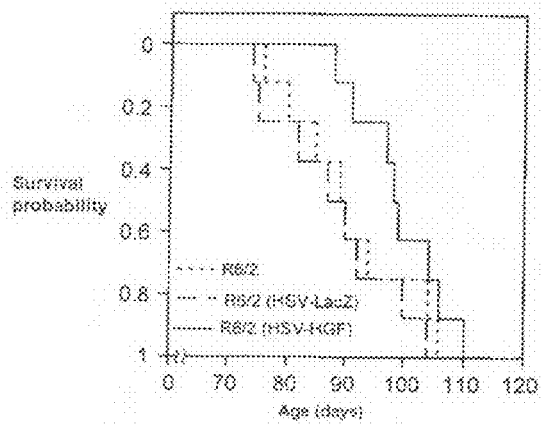
FIG. 3 shows the survival curve of R6/2 mice in which HSV-HGF or HSV-LacZ was transferred into the striatum.

The result is shown in FIG. 3. The average lifespan of R6/2(HSV-HGF) mice was 100.4±2.6 days, which exceeded the average lifespan of 91.3±3.8 days for R6/2 mice and 88.6±3.8 days for R6/2 (HSV-LacZ) mice due to the HSV-HGF injection into R6/2 mice.

11. Effect of HGF on Clasping Test

For the clasping test, mice were suspended by the tails for 30 seconds and the duration of a foot clasping (a posture in which mice are unable to stretch their limbs) was scored.

The duration of the foot clasping was scored in accordance with the method of Tanaka, M. et al. (see also Nat. Med, vol. 10, pp. 148-154, Epub. 2004, January 2018), based on the duration of the foot clasping as shown in Table 1.

TABLE 1

| Score | Duration of Foot clasping (sec) |
|---|---|
| 3 | 10 or more |
| 2 | 5 to 10 |

TABLE 1-continued

| Score | Duration of Foot clasping (sec) |
|---|---|
| 1 | 0 to 5 |
| 0 | 0 |

Figure 4:
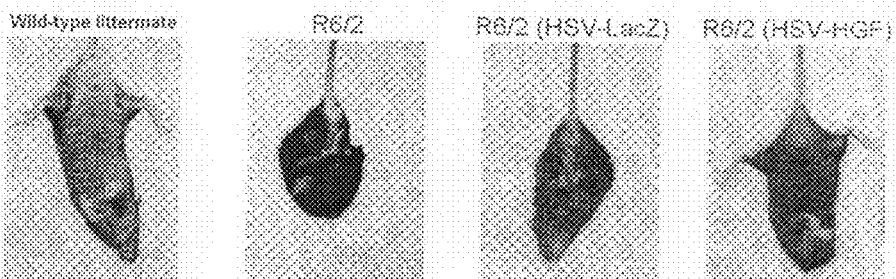
FIG. 4 shows mouse behaviors in the clasping test.
Figure 5:
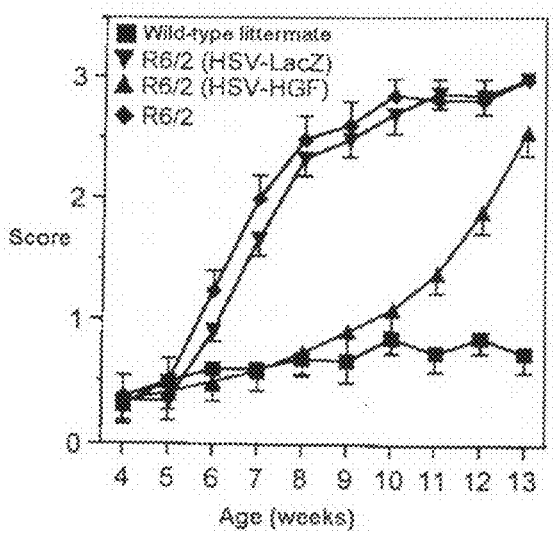
FIG. 5 shows the time-course in score of the clasping test.

The R6/2 mouse behavior shown in FIG. 4 demonstrates a typical foot clasping phenotype. Such a phenotype was not shown in wild-type littermate mice (FIG. 4: wild-type littermate). The time-course in foot clasping score is shown in FIG. 5. The foot clasping phenotype continued to be observed in R6/2 or R6/2(HSV-LacZ) mice at or after 6 weeks of age. The foot clasping phenotype was not observed in R6/2 (HSV-HGF) mice until at 8 weeks of age, and even after this, the foot clasping score continued to be restrained until at 12 weeks of age.

12. Effect of HGF in the Rotarod Test

The rotarod apparatus was used for measurement of forelimb and hindlimb motor coordination and balance. The rotarod test was performed in compliance with the method of Ferrante, R. J. et al. (cf. J. Neurosci., 2000, vol. 20, pp. 4389-4397). Namely, the test was conducted by using the rotarod apparatus and each mouse was placed on a rod rotating at 10 rpm for a maximum of 180 seconds, and the latency to fall off the rotating rod within this time was recorded and then analyzed.

Figure 6:
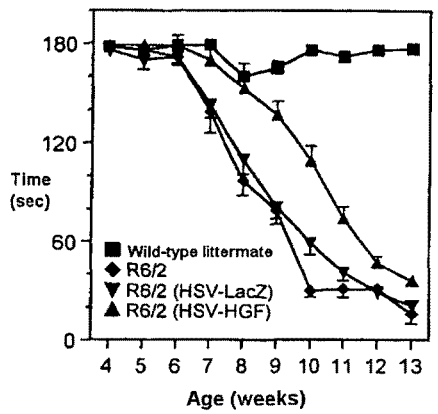
FIG. 6 shows the time-course in motor function in the rotarod test.

The time-course in the rotarod test is shown in FIG. 6. The motor coordination and balance of mice in the rotarod test was deteriorated in a time-dependent manner in R6/2 and R6/2 (HSV-LacZ) mice compared with wild-type littermate mice. The performance in the rotarod test was significantly improved in R6/2(HSV-HGF) mice compared with R6/2 and R6/2(HSV-LacZ) mice.

13. Effect of HGF in the Footprint Test

The footprint test was performed in compliance with the method of Carter, R. J. et al. (cf. J. Neurosci., 1999, vol. 19, pp. 3248-3257). To analyze footprinting patterns, fore- and hindlimb movements during walking were recorded with a red (for forefeet) and black (for hindfeet) ink in accordance with the method of Carter, R. J. et al. Animals were allowed to walk along a 50-cm-long and 10-cm-wide runway. A stride distance was measured as the average distance of forelimb movement between each stride. An overlap between left or right front footprint and hind footprint was used to measure uniformity of stride alteration.

Figure 7:
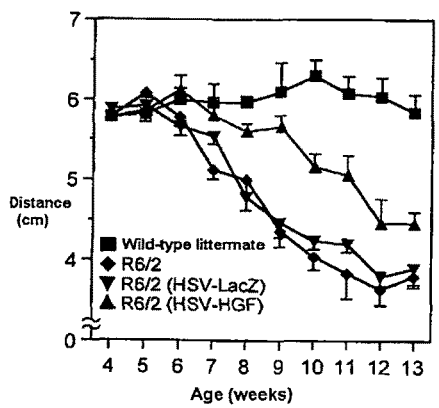
FIG. 7 shows the time-course in average stride distance in the footprint test.
Figure 8:
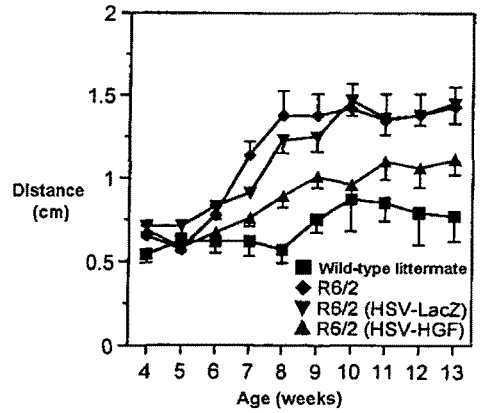
FIG. 8 shows the time-course in separation of the front footprint/hind footprint overlap in the footprint test.

The time-course in the footprint test are shown in FIGS. 7 and 8. In R6/2 and R6/2(HSV-LacZ) mice compared with wild-type littermate mice, the stride distance was decreased and the forelimb/hindlimb overlap was disrupted in a time-dependent manner, and the front footprint and hind footprint were separated. In R6/2(HSV-HGF) mice, the stride distance was increased (FIG. 7) and the disruption of the forelimb/hindlimb overlap was inhibited compared with R6/2 mice (FIG. 8).

14. Result of Histological and Immunohistochemical Analysis

Results of histological and immunohistochemical analysis are shown as follows.

(1) Brain Atrophy and Brain Weight

Figure 9:
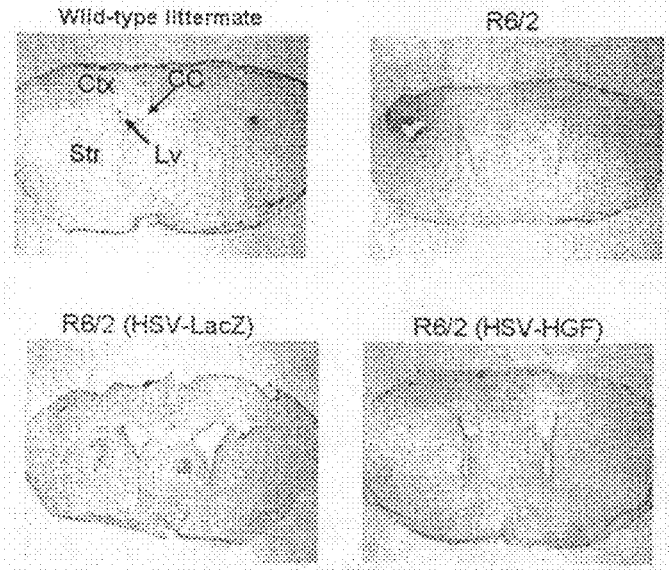
FIG. 9 shows mouse brain coronal sections. Ctx, CC, Str and Lv represent cerebral cortex, corpus callosum, striatum and lateral ventricle, respectively.
Figure 10:
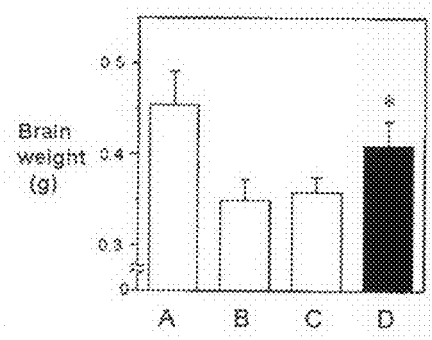
FIG. 10 shows the brain weight of 9-week-old mice. A, B, C and D show wild-type littermate mice, R6/2 mice, R6/2 (HSV-LacZ) mice and R6/2(HSV-HGF) mice, respectively.

The present inventors evaluated the effect of HGF on brain atrophy in R6/2 mice by employing the Nissl staining method for brain regions (FIG. 9). Ventricular dilatation caused by striatal atrophy was observed in 9-week-old R6/2 and R6/2 (HSV-LacZ) mice. Meanwhile, the ventricular dilatation was inhibited in R6/2(HSV-HGF) mice. The brain weight of 9-week-old mice is shown in FIG. 10. The brain weight was decreased in R6/2 and R6/2(HSV-LacZ) mice compared with wild-type littermate mice. However, the decrease in brain weight was inhibited in R6/2(HSV-HGF) mice.

(2) Effect of HGF on NeuN Positive Cell Count

Figure 11:
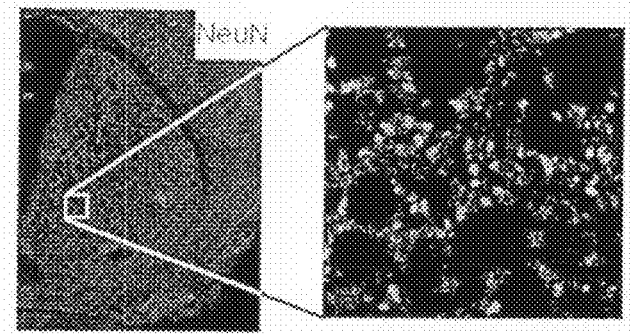
FIG. 11 shows NeuN positive cells in the striatum.
Figure 12:
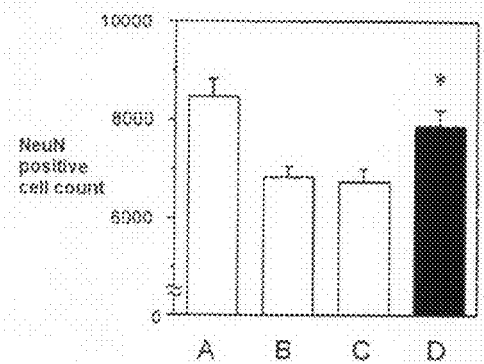
FIG. 12 shows NeuN positive cell counts in the striatum. A, B, C and D show wild-type littermate mice, R6/2 mice, R6/2 (HSV-LacZ) mice and R6/2(HSV-HGF) mice, respectively.

The total count of neurons in the striatum of 9-week-old mice was determined using NeuN, a marker for a neuron, as an indicator. NeuN was detected by immunohistochemical staining using anti-NeuN antibody (FIG. 11) and the detected cells (NeuN positive cells) were counted (FIG. 12). NeuN positive cell count was significantly decreased in R6/2 and R6/2(HSV-LacZ) mice compared with wild-type littermate mice. In R6/2(HSV-HGF) mice, NeuN positive cell count was significantly increased compared with R6/2 and R6/2(HSV-LacZ) mice.

(3) Effect of HGF on Phosphorylated c-Met

Figure 13:
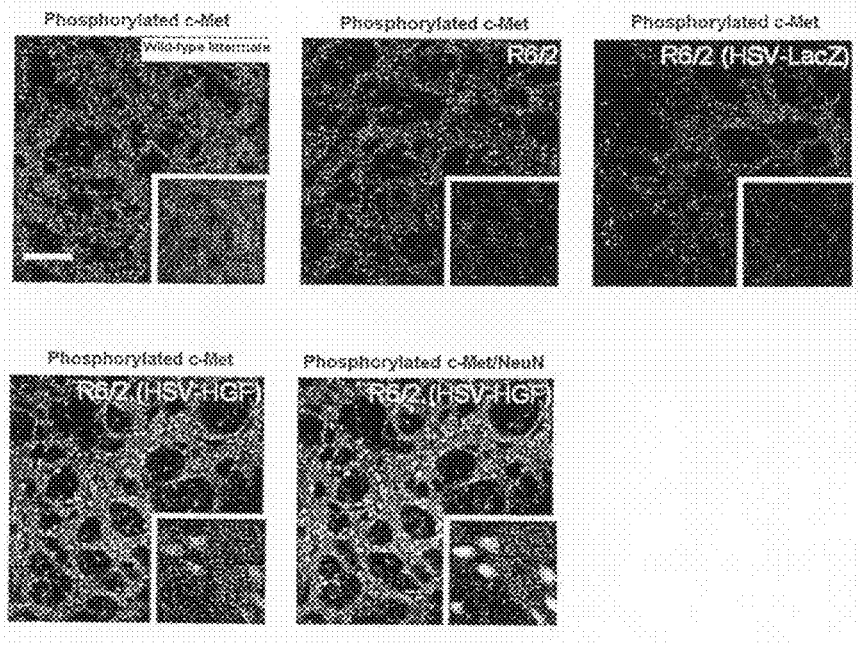
FIG. 13 shows the phosphorylated c-Met expression in the striatum.

By using R6/2 mice, it was elucidated whether c-Met/HGF receptor was expressed in the mice. The immunohistochemical analysis shows that the c-Met/HGF receptor was localized in NeuN positive cells in R6/2 mice as well as wild-type littermate mice (FIG. 13; phosphorylated c-Met/NeuN). The present inventors performed immunostaining for phosphorylated c-Met in the striatum to study the HGF-induced c-Met tyrosine phosphorylation (FIG. 13). The phosphorylated c-Met immunoactivity level, which reflects the c-Met activation, was significantly enhanced in R6/2 (HSV-HGF) mice compared with mice in the other groups.

(4) Effect of HGF on Caspase

In Huntington's disease, caspase-3 has been reported to be activated (see also Zhang, Y. et al., J. Neurochem., 2003, vol. 87, pp. 1184-1192). The present inventors examined whether HGF affected the activation of caspase-3 to explore the neuroprotective effect of HGF. The present inventors assessed the effect of HSV-HGF on the caspase activation in the striatum using immunostaining for active caspase-3.

Figure 14:
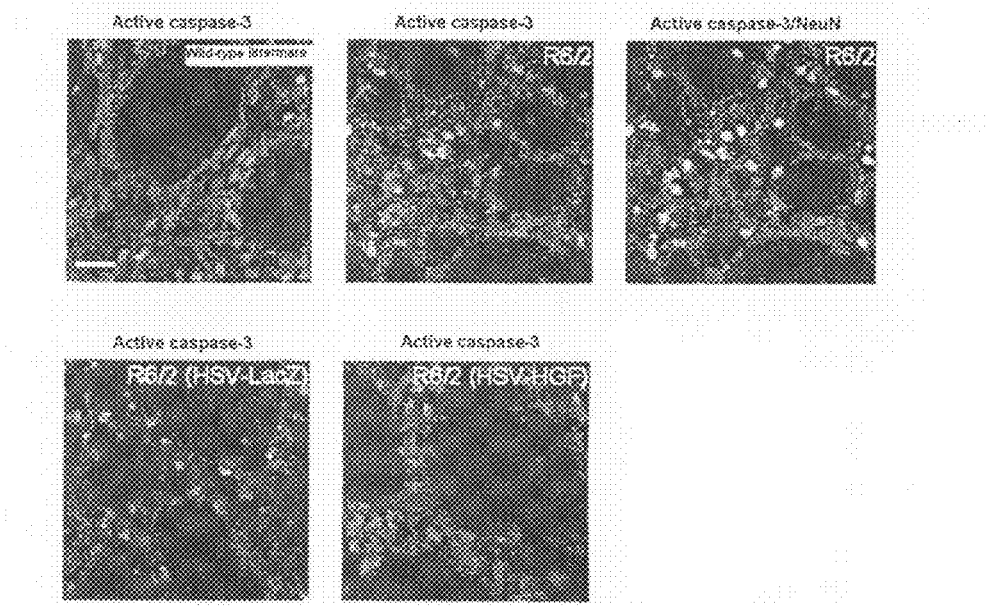
FIG. 14 shows the immunostaining images of active caspase-3 in the striatum.

Results of immunohistochemical analysis in 9-week-old mice are shown as follows. Namely, active caspase-3 was observed in the striatum of R6/2 and R6/2 (HSV-LacZ) mice (mainly in NeuN positive cells; FIG. 14; active caspase-3/NeuN), but it was not observed in the striatum of wild-type littermate mice. The immunoactivity of the active caspase-3 was decreased in R6/2(HSV-HGF) mice (FIG. 14).

Figure 15:
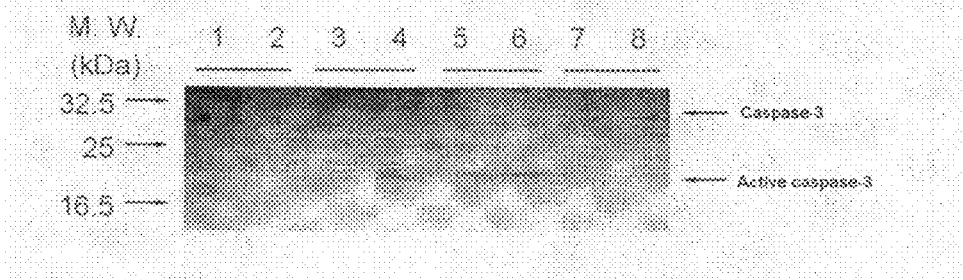
FIG. 15 shows the result of western blot analysis for caspase-3. Lanes 1 and 2 show wild-type littermate mice, lanes 3 and 4 show R6/2 mice, lanes 5 and 6 show R6/2(HSV-LacZ) mice and lanes 7 and 8 show R6/2(HSV-HGF) mice.
Figure 16:
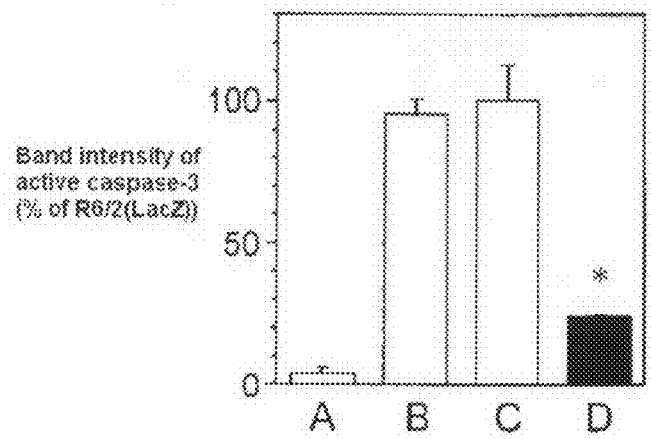
FIG. 16 shows the band intensity of active caspase-3 in western blot analysis. A, B, C and D show wild-type littermate mice, R6/2 mice, R6/2 (HSV-LacZ) mice and R6/2 (HSV-HGF) mice, respectively.
Figure 17:
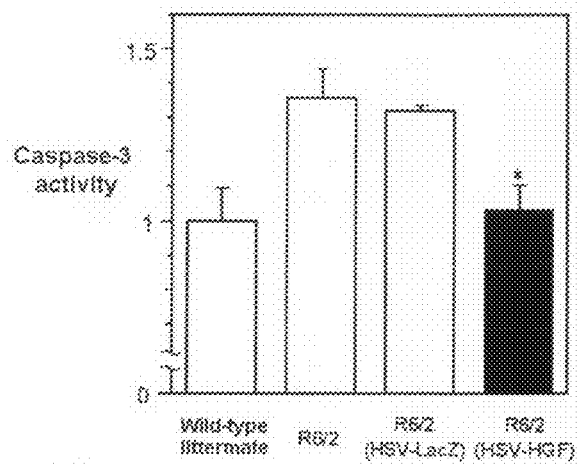
FIG. 17 shows the activation rate of caspase-3 in R6/2 mice compared with wild-type littermate mice.

Western blot analysis was performed to quantify the active caspase-3 (FIG. 15). A remarkable activation of caspase-3 was observed in R6/2(HSV-LacZ) mice. Meanwhile, the caspase-3 activation was inhibited in R6/2(HSV-HGF) mice compared with R6/2 and R6/2 (HSV-LacZ) mice. As shown by the quantitative band intensity of active caspase-3 in western blot analysis, the caspase-3 activation was inhibited to 23% in R6/2(HSV-HGF) mice, with the caspase-3 activation set to 100% in R6/2(HSV-LacZ) mice (FIG. 16). A similar result was given in the measurement of caspase-3 activity (FIG. 17). The caspase-3 activity was higher in R6/2 and R6/2(HSV-LacZ) mice than in wild-type littermate mice. Meanwhile, in R6/2(HSV-HGF) mice, the caspase-3 activity was inhibited to the same level as in wild-type littermate mice.

Figure 18:
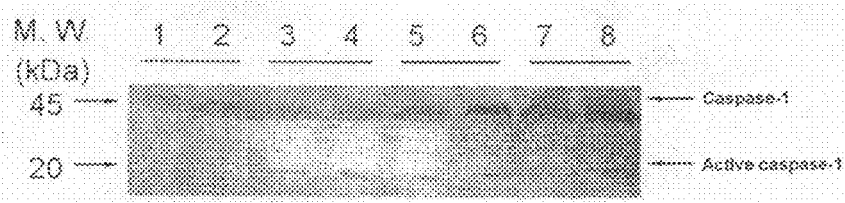
FIG. 18 shows the result of western blot analysis for caspase-1. Lanes 1 and 2 show wild-type littermate mice, lanes 3 and 4 show R6/2 mice, lanes 5 and 6 show R6/2(HSV-LacZ) mice, and lanes 7 and 8 show R6/2(HSV-HGF) mice.
Figure 19:
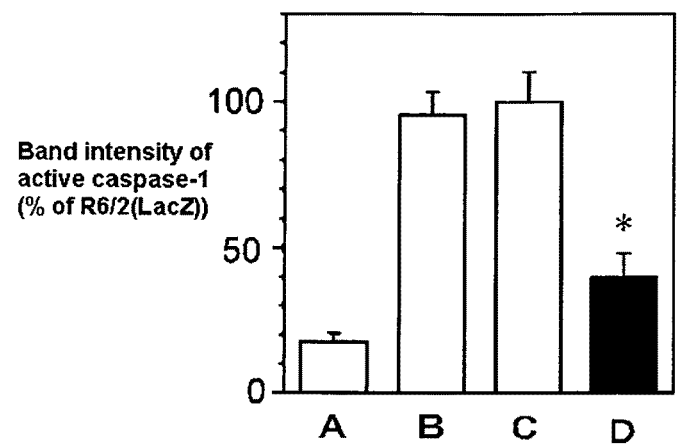
FIG. 19 shows the band intensity of active caspase-1 in western blot analysis. A, B, C and D show wild-type littermate mice, R6/2 mice, R6/2(HSV-LacZ) mice and R6/2 (HSV-HGF) mice, respectively.
Figure 20:
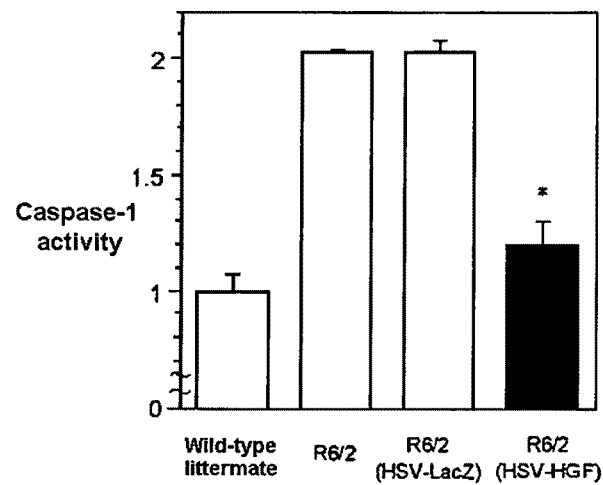
FIG. 20 shows the activation rate of caspase-1 in R6/2 mice compared with wild-type littermate mice.

Furthermore, caspase-1 has been reported to be activated in the brain of Huntington's disease patients and R6/2 mice (cf. Zhang, Y. et al., J. Neurochem., 2003, vol. 87, pp. 1184-1192). In this context, caspase-1 in the striatum of R6/2 mice was examined by western blot analysis (FIG. 18). Western blot analysis for caspase-1 was performed using respective antibodies recognizing a pro- or active-form of caspase-1. As measured by western blot analysis, the band intensity of active caspase-1 (% of R6/2(HSV-LacZ) mice) was inhibited to 40% in the striatum of R6/2(HSV-HGF) mice (FIG. 19). A similar result was given in the measurement of caspase-1 activity (FIG. 20). The caspase-1 activity was higher in R6/2 and R6/2(HSV-LacZ) mice than in wild-type littermate mice. Meanwhile, in R6/2(HSV-HGF) mice, the caspase-1 activity was inhibited to the same level as in wild-type littermate mice.

Test Example 2

Effect of HGF on Neurogenesis in the Brain of Huntington's Disease Transgenic Mice For use in the following experiments, R6/2 mice, R6/2 (HSV-LacZ) mice, R6/2(HSV-HGF) mice and wild-type littermate mice were prepared in the same manner as in Test Example 1.

1. Effect of HGF on Ki-67 Cells

Figure 21:
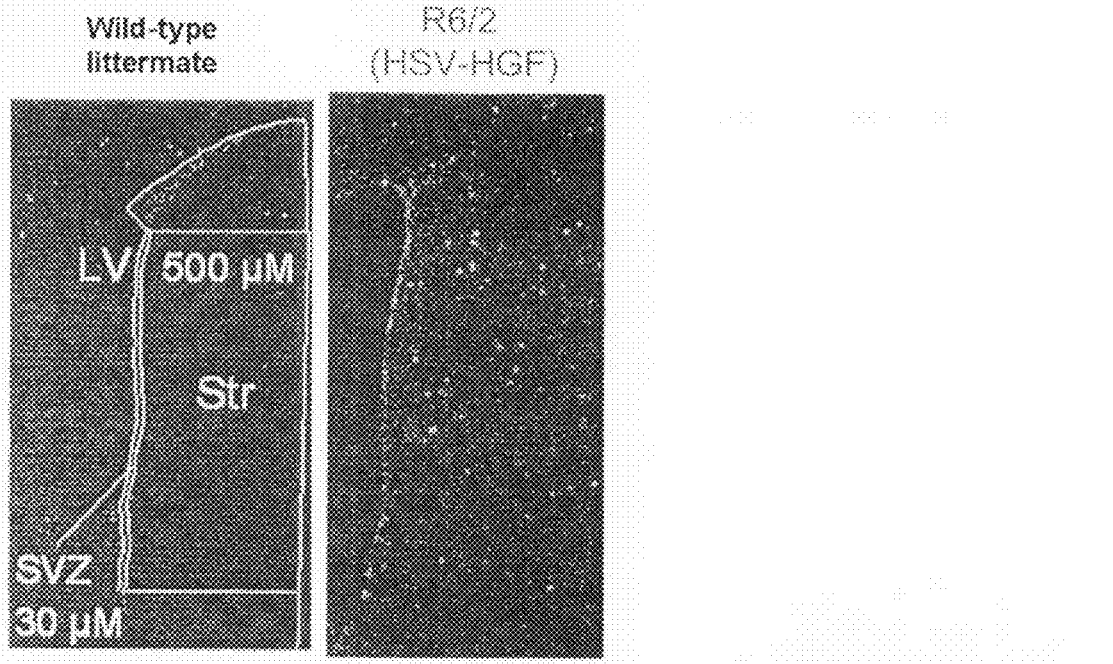
FIG. 21 shows the immunostaining images of Ki-67 positive cell in the striatum of R6/2(HSV-HGF) mice and wild-type littermate mice. Str, LV and SVZ represent striatum, lateral ventricle and subventricular zone, respectively.

Proliferation of neurons in the subventricular zone (SVZ) and striatum was examined. Ki-67 was selected as a marker for a proliferating cell and immunostaining for Ki-67 was performed. Ki-67 positive cells in the SVZ and striatum were counted. Ki-67 positive cell count was significantly increased in the striatum of R6/2(HSV-HGF) mice compared with R6/2 mice and R6/2(HSV-LacZ) mice (FIG. 21).

2. Effect of HGF on BrdU Uptake

Five-week-old mice were intraperitoneally administered with 75 mg/kg BrdU (dissolved in saline) every 2 hours for 4 times and killed at the 28th day post-injection of BrdU (i.e., at 9 weeks of age). The mice were anesthetized and perfused transcardially with PBS followed by PBS containing 4% paraformaldehyde for fixation. The brain was cryoprotected stepwise with 10% and 20% sucrose, and then frozen. The frozen brain was serially sectioned at a thickness of 20 μm.

For immunohistochemical staining for BrdU, the cryosections were incubated with 1N hydrochloric acid at 60° C. for 30 minutes and then were soaked in PBS supplemented with 10% goat serum for 1 hour. Subsequently, the cryosections were incubated with anti-BrdU antibody (rat monoclonal antibody; manufactured by Oxford Biotechnology; Cat No. OBT0030) at 4° C. for 36 hours. For double staining, the cryosections were incubated with the secondary antibody conjugated to fluorescent dyes Alexa 488 and Alexa 546 (manufactured by Molecular Probes) to visualize BrdU, and the cryosections were counterstained for nucleus with TO PRO-3 (manufactured by Molecular Probes). Fluorescent images were obtained by Zeiss LSM-510 confocal fluorescence microscope.

Figure 22:
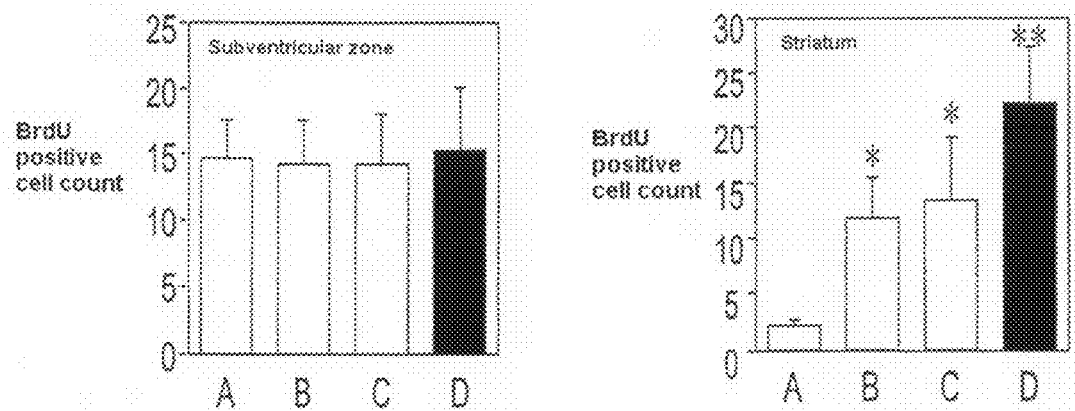
FIG. 22 shows BrdU-positive cell counts in mouse SVZ and striatum. A, B, C and D show wild-type littermate mice, R6/2 mice, R6/2 (HSV-LacZ) mice and R6/2(HSV-HGF) mice, respectively. * indicates significant difference from wild-type littermate mice ($p<0.05$) and ** indicates significant difference from R6/2(HSV-LacZ) mice ($p<0.05$).

Results:

As a result of measurement of BrdU-positive cell in the SVZ and striatum, no group significant differences were observed in BrdU-positive cell count in the SVZ. However, BrdU-positive cell count was significantly increased in the striatum of R6/2(HSV-HGF) mice compared with R6/2 mice and R6/2(HSV-LacZ) mice (FIG. 22). These data show that the HSV-HGF treatment enhances the proliferation of neurons.

3. Effect of HGF on Nestin/BrdU-Positive Cells

Figure 23:
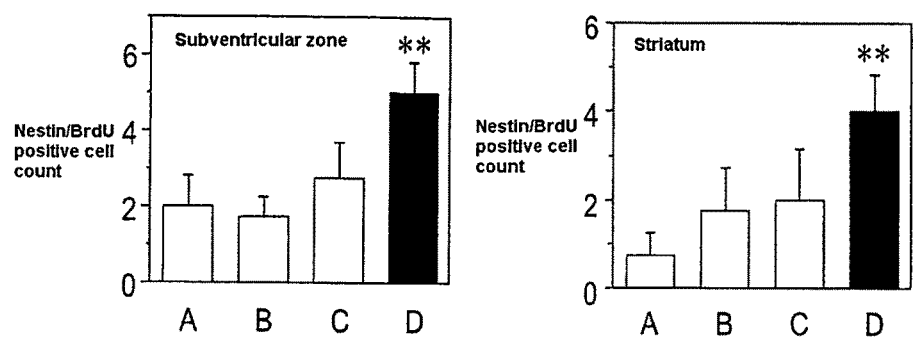
FIG. 23 shows the numbers of cells positive for Nestin and BrdU in mouse SVZ and striatum. A, B, C and D show wild-type littermate mice, R6/2 mice, R6/2(HSV-LacZ) mice and R6/2(HSV-HGF) mice, respectively. ** indicates significant difference from R6/2(HSV-LacZ) mice ($p<0.05$).

Nestin is a marker for a neural stem cell. Nestin was stained in accordance with the immunohistochemical staining method described in Test Example 1. For an antibody for Nestin, anti-Nestin antibody (mouse polyclonal antibody; manufactured by BD Biosciences; Cat No. 556309) was diluted 100-fold for use. Cells positive for Nestin and BrdU were counted. The Nestin/BrdU-positive cell count was significantly increased in the SVZ and striatum of R6/2(HSV-HGF) mice compared with R6/2 mice and R6/2(HSV-LacZ) mice (FIG. 23).

4. Effect of HGF on DCX/BrdU-Positive Cells

Doublecortin (DCX) is a marker for a migrant neuroblast. DCX was stained in accordance with the immunohistochemical staining method described in Test Example 1. For an antibody for DCX, anti-DCX antibody (goat polyclonal antibody; manufactured by Santa Cruz Biotechnology; Cat No. sc-8066) was diluted 100-fold for use.

Figure 24:
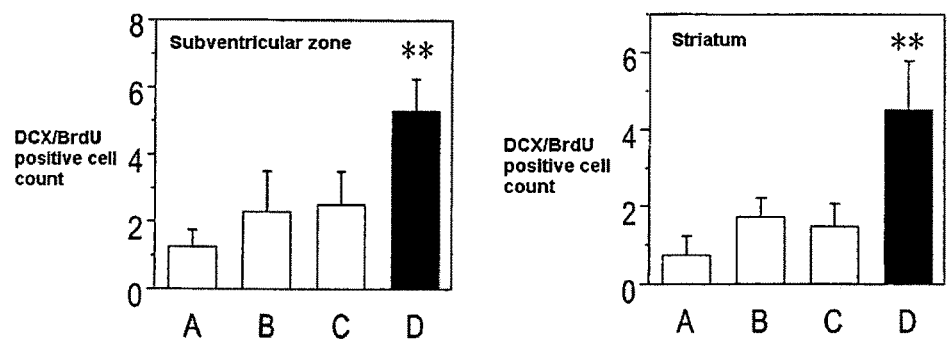
FIG. 24 shows the numbers of cells positive for DCX and BrdU in mouse SVZ and striatum. A, B, C and D show wild-type littermate mice, R6/2 mice, R6/2(HSV-LacZ) mice and R6/2(HSV-HGF) mice, respectively. ** indicates significant difference from R6/2(HSV-LacZ) mice ($p<0.05$).

Cells positive for DCX and BrdU were counted. The DCX/BrdU-positive cell count was significantly increased in the SVZ and striatum of R6/2(HSV-HGF) mice compared with R6/2 mice and R6/2(HSV-LacZ) mice (FIG. 24).

5. Effect of HGF on PSA-NCAM/BrdU-Positive Cells

PSA-NCAM is a marker for a migrant neuroblast. PSA-NCAM was stained in accordance with the immunohistochemical staining method described in Test Example 1. For an antibody for PSA-NCAM, anti-PSA-NCAM antibody (mouse monoclonal antibody; manufactured by AbCys S.A.; Cat No. AbC0019) was diluted 800-fold for use.

Figure 25:
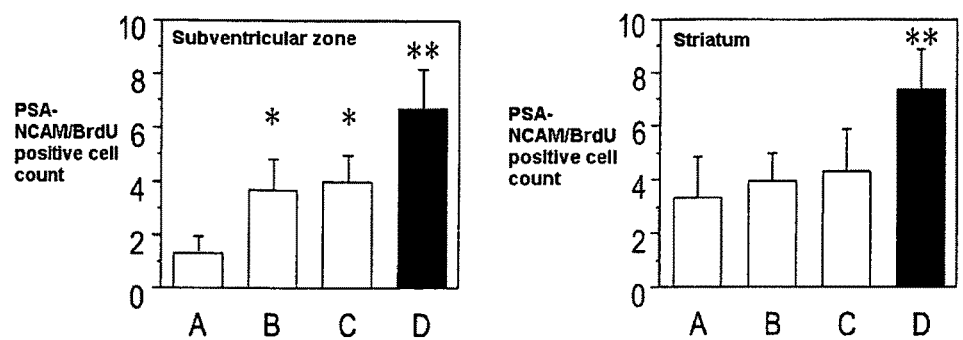
FIG. 25 shows the numbers of cells positive for PSA-NCAM and BrdU in mouse SVZ and striatum. A, B, C and D show wild-type littermate mice, R6/2 mice, R6/2(HSV-LacZ) mice and R6/2(HSV-HGF) mice, respectively. * indicates significant difference from wild-type littermate mice ($p<0.05$) and ** indicates significant difference from R6/2 (HSV-LacZ) mice ($p<0.05$).

Cells positive for PSA-NCAM and BrdU were counted. The PSA-NCAM/BrdU-positive cell count was significantly increased in the SVZ and striatum of R6/2(HSV-HGF) mice compared with R6/2 mice and R6/2(HSV-LacZ) mice (FIG. 25).

6. Effect of HGF on βIII Tubulin/BrdU Positive Cells

βIII tubulin is a marker for a neuron between the early stage and differentiation stage. βIII tubulin was stained in accordance with the immunohistochemical staining method described in Test Example 1. For an antibody for βIII tubulin, anti-β-III tublin antibody (TuJ1, mouse monoclonal antibody; manufactured by R&D Systems; Cat No. MAB1195) was diluted 200-fold for use.

Figure 26:
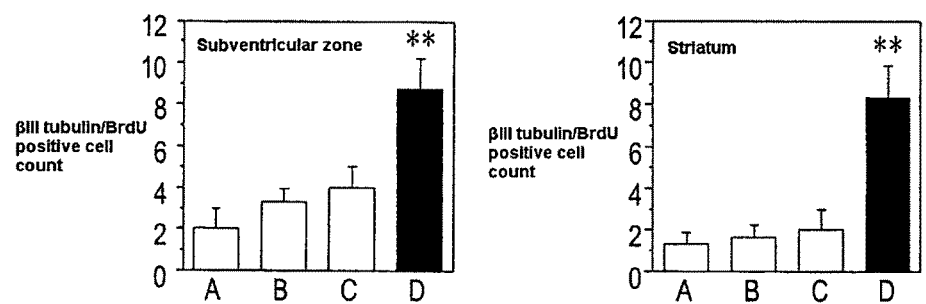
FIG. 26 shows the numbers of cells positive for βIII tubulin and BrdU in mouse SVZ and striatum. A, B, C and D show wild-type littermate mice, R6/2 mice, R6/2(HSV-LacZ) mice and R6/2(HSV-HGF) mice, respectively. ** indicates significant difference from R6/2(HSV-LacZ) mice ($p<0.05$).

Cells positive for βIII tubulin and BrdU were counted. The βIII tubulin/BrdU-positive cell count was significantly increased in the SVZ and striatum of R6/2 (HSV-HGF) mice compared with R6/2 mice and R6/2(HSV-LacZ) mice (FIG. 26).

7. Effect of HGF on NeuN/BrdU-Positive Cells

NeuN is a marker for a differentiated neuron. NeuN was immunochemically stained using the same antibody as described in Test Example 1 in the same manner as in Test Example 1.

Figure 27:
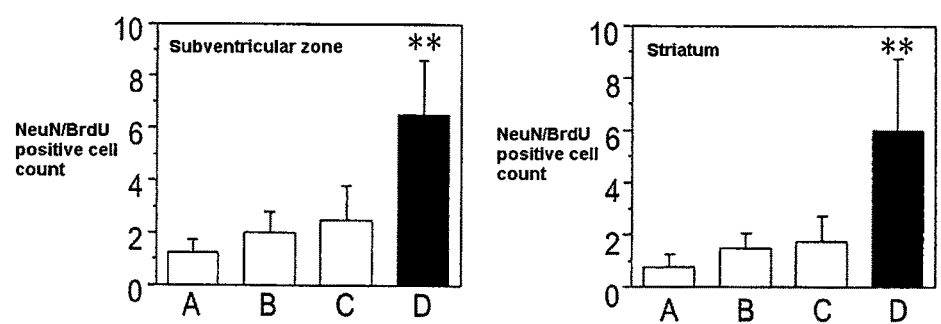
FIG. 27 shows the numbers of cells positive for NeuN and BrdU in mouse SVZ and striatum. A, B, C and D show wild-type littermate mice, R6/2 mice, R6/2(HSV-LacZ) mice and R6/2(HSV-HGF) mice. ** indicates significant difference from R6/2(HSV-LacZ) mice ($p<0.05$).

Cells positive for NeuN and BrdU were counted. The NeuN/BrdU-positive cell count was significantly increased in the SVZ and striatum of R6/2(HSV-HGF) mice compared with R6/2 mice and R6/2(HSV-LacZ) mice (FIG. 27).

8. Effect of HGF on Phosphorylated c-Met/Nestin-Positive Cells

To study a role of HGF on neurogenesis, it was examined whether HGF affected c-Met tyrosine phosphorylation in Nestin-positive cells. Phosphorylated c-Met and Nestin were immunochemically stained using the same antibodies as described in Test Example 1 in the same manner as in Test Example 1.

Figure 28:
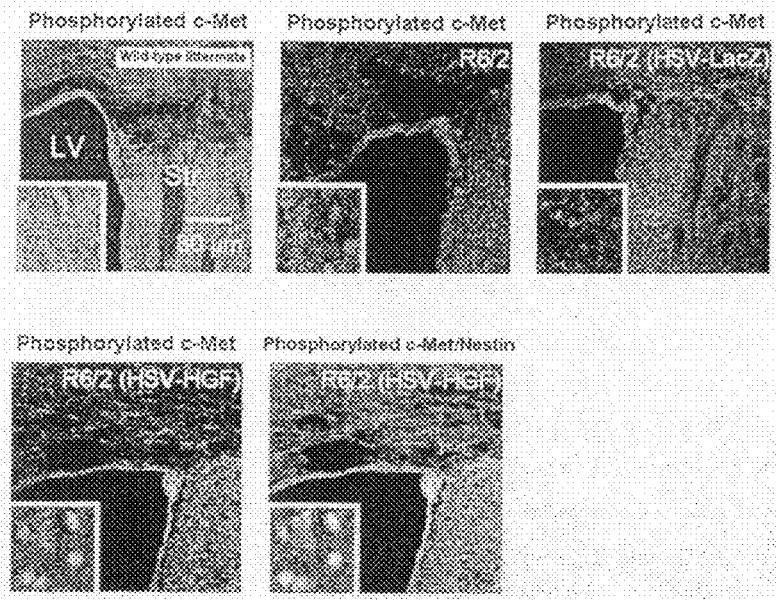
FIG. 28 shows the immunostaining images of cells positive for Nestin and phosphorylated c-Met in mouse striatum.

The phosphorylated c-Met/Nestin-positive cell count was significantly increased in R6/2(HSV-HGF) mice compared with mice in the other groups (FIG. 28).

9. Effect of HGF on Phosphorylated c-Met/DCX Positive Cells

To study a role of HGF on neurogenesis, it was examined whether HGF affected c-Met tyrosine phosphorylation in DCX-positive cells. Phosphorylated c-Met and DCX were immunochemically stained in the same manner as above.

Figure 29:
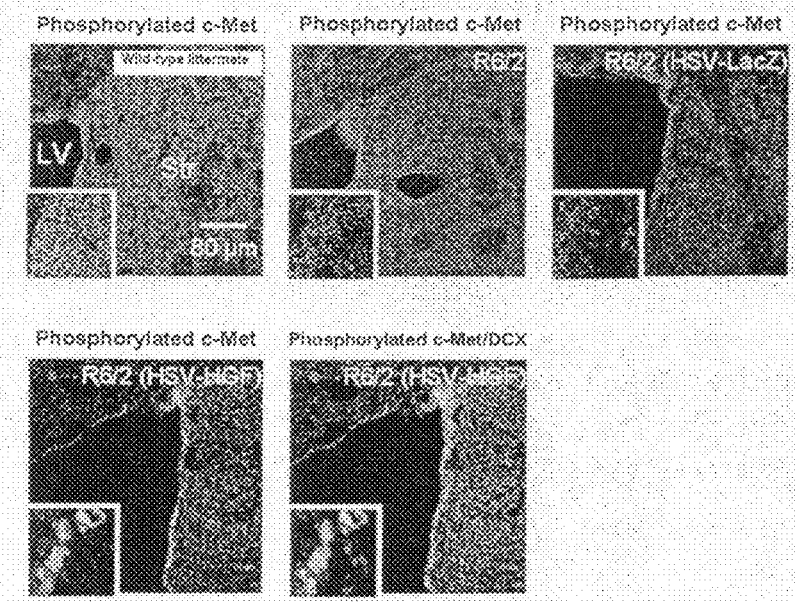
FIG. 29 shows the immunostaining images of cells positive for DCX and phosphorylated c-Met in mouse striatum.

The phosphorylated c-Met/DCX-positive cell count was significantly increased in R6/2(HSV-HGF) mice compared with mice in the other groups (FIG. 29).

Test Example 3

HGF Expression in the Spinal Cord Administered with a Vector Containing DNA Encoding HGF Protein 1. Construction, Preparation and Purification of the Vector
(1) HSV-1 Vector Inserted with DNA Encoding for HGF Protein As herpes simplex virus type 1 (HSV-1) inserted with HGF gene, HSV1764/-4/pR19HGF viral vector prepared in Test Example 1 was used. Hereinafter, the vector was abbreviated as HSV-HGF.

(2) AAV-2 and AAV-4 Vectors Inserted with DNA Encoding for HGF Protein

Rat HGF-KT3 (DNA encoding rat HGF (SEQ ID NO: 5) tagged with KT3 epitope (3'-CCGCCCGAGCCAGAGACT-5'; SEQ ID NO: 7) at the C-terminus; Sun, W., Funakoshi, H. et al., J. Neurosci., 2002, vol. 22, pp. 6537-6548) was inserted into the multi-cloning site of pCMV-MCS, which is contained in AAV Helper-Free System Kit (Stratagene, USA; Cat No. #240071). Sequence analysis proved that this insertion had been correctly carried out. This vector was cleaved at NotI sites to give two fragments and the fragment having rat HGF-KT3 was inserted in replacement of a corresponding fragment given by cleaving pAAV-MCS in the same manner, to prepare pAAV-ratHGF-KT3 for later preparation of AAV2-HGF. For later preparation of AAV4-HGF, pAAV-MCS modified for AAV4 was used to prepare pAAV$^4$-ratHGF-KT3 (cf. Proc. Natl. Acad. Sci. USA, 2000, vol. 97, pp. 3428-3432). Subsequently, pAAV-MCS inserted with ratHGF-KT3 was transfected into HEK193 contained in the above-mentioned kit in accordance with the instruction manual. The expression and activity of ratHGF-KT3 in the cell were confirmed by ELISA and MDCK cell scattering assay. The resulting vectors are abbreviated as AAV2-HGF and AAV4-HGF.

2. HGF Expression Induced by Administration into the Spinal Parenchyma

5 µl of a vector suspension (HSV-HGF: $3\times10^7$ pfu, $3\times10^7$ pfu; AAV2-HGF: $3\times10^{11}$ pfu; or AAV4-HGF: $3\times10^{11}$ pfu) was stereotaxically injected into the spinal parenchyma of lumbar cord of adult female SD rats using a minipump. Five days later, the rats were deeply anesthetized with pentobarbital and then killed. Immediately after this, the spinal cord was isolated and divided into the three regions: upper spinal region (U), middle spinal region (M) and lower spinal region (L). Each region was homogenized in the above-mentioned manner. HGF protein levels were measured by ELISA.

Figure 30:
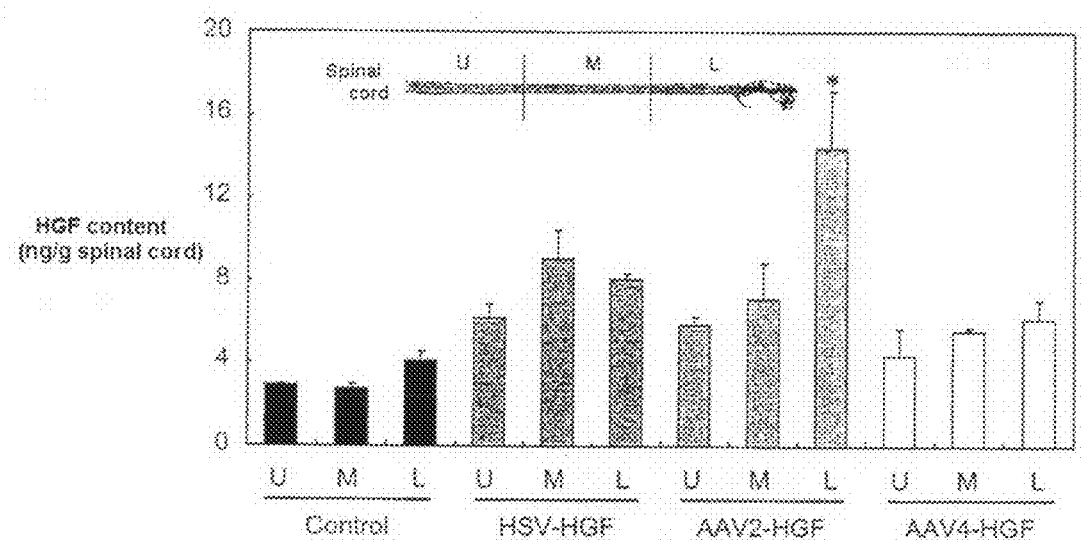
FIG. 30 shows the HGF expression levels in the spinal cord 5 days after injection of three respective vectors inserted with DNA encoding HGF protein (HSV-HGF, AAV2-HGF and AAV4-HGF) into the rat spinal parenchyma of lumbar cord. U, M and L show the upper, middle and lower spinal regions, respectively. * indicates significant difference from control ($p<0.05$).

The results are shown in FIG. 30. After the injection of the vector into the spinal parenchyma of lumbar cord, HGF expression was observed in the upper and middle spinal regions as well as in the injected area. The order of the HGF expression intensity is lower spinal region (including the lumbar cord)>=middle spinal region>upper spinal region. In addition, the injection of HSV-HGF vector increased the HGF expression in a dose-dependent manner.

3. HGF Expression Induced by Administration into the Medullary Cavity

5 µl of a vector suspension (HSV-HGF: $3\times10^7$ pfu, $3\times10^7$ pfu; AAV2-HGF: $3\times10^{11}$ pfu; or AAV4-HGF: $3\times10^{11}$ pfu) was stereotaxically injected into the medullary cavity of lumbar cord of adult female SD rats using a minipump. Five days later, the spinal cord was isolated in the same manner as in the above-mentioned "administration into the spinal parenchyma", and then HGF protein levels in the upper, middle and lower spinal regions were determined.

Figure 31:
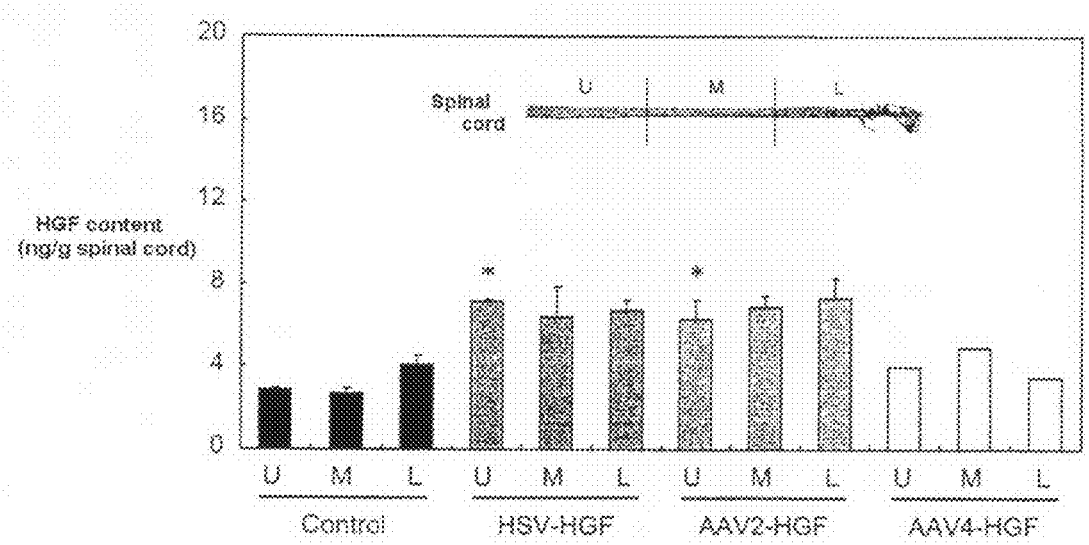
FIG. 31 shows the HGF expression levels in the spinal cord 5 days after injection of three respective vectors inserted with DNA encoding HGF protein (HSV-HGF, AAV2-HGF and AAV4-HGF) into the rat medullary cavity of lumbar cord. U, M and L show the upper, middle and lower spinal regions, respectively. * indicates significant difference from control ($p<0.05$).

The results are shown in FIG. 31. After the injection of the vector into the medullary cavity of lumbar cord, HGF expression was observed in the upper and middle spinal regions as well as in the injected area. The intensity of HGF expression was lower than the corresponding intensity upon injection into the spinal parenchyma, but the intensity levels were almost the same in the upper, middle and lower (including the lumbar cord) spinal regions. Namely, the intrathecal administration was able to supply HGF to neurons over a wider region. The reason for this is considered that the spinal fluid helped the wider spread of the vector all over the spinal cord than in the case of administration into the spinal parenchyma. In addition, the injection of HSV-HGF vector increased the HGF expression in a dose-dependent manner.

Test Example 4

Effect of HGF on the Processing of Gene Product Resulting from Mutant HD Exon 1

For use in the following experiments, R6/2 mice, R6/2 (HSV-LacZ) mice, R6/2(HSV-HGF) mice and wild-type littermate mice were prepared in the same manner as in Test Example 1. Nine-week-old mice in each group were killed and the striatal homogenates were prepared in the same manner as described in the above-mentioned "western blot" of Test Example 1. Then, after separation of proteins by SDS-PAGE, the separated proteins were electrotransferred to PVDF membrane. The protein-transferred PVDF membrane was blocked with 10 mass % fat-free milk at room temperature for 2 hours and was blotted with anti-huntingtin antibody. The anti-huntingtin antibody (goat polyclonal antibody; manufactured by Santa Cruz; Cat No. sc-8678), which recognizes a C-terminal region of huntingtin protein, was diluted 100-fold for use. Subsequently, after incubation with a secondary antibody (manufactured by DakoCytomation) conjugated to horseradish peroxidase (HRP), the membrane was developed with ECL reagents (Cat No. RPN2106, manufactured by Amersham Biosciences) in accordance with the product manual.

The band intensity was analyzed by NIH (National Institutes of Health) imaging software developed by Wayre Rasband.

Figure 32:
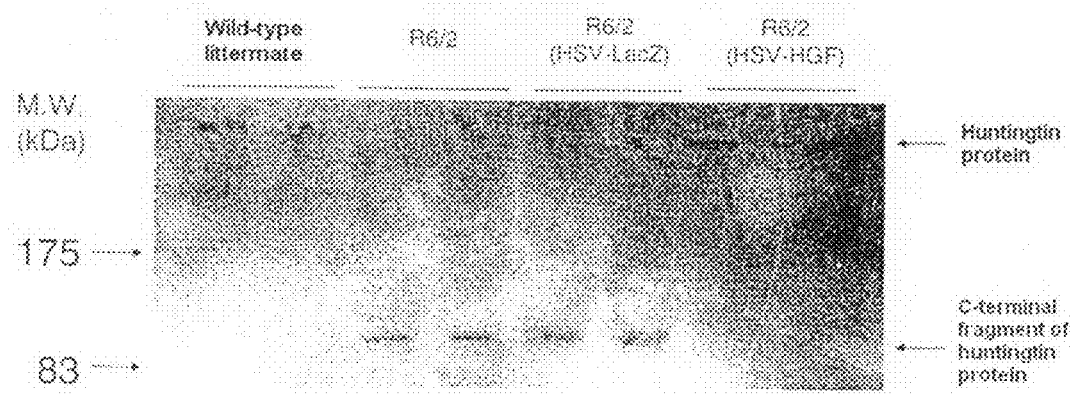
FIG. 32 shows the result of western blot analysis for huntingtin protein.

The result of western blot analysis is shown in FIG. 32. In wild-type littermate mice, the expression of huntingtin protein was observed, but few C-terminal fragments were detected. In R6/2 mice compared with wild-type littermate mice, little band was detected in the site corresponding to huntingtin protein, and the C-terminal fragment derived from the protein was strongly detected. This result shows that huntingtin protein is fragmented by processing of the gene product derived from mutant HD exon 1 in R6/2 mice. HSV-LacZ-treated R6/2 mice also show a similar result to R6/2 mice. On the other hand, in HSV-HGF-treated R6/2 mice, the band was detected in the same site as huntingtin protein detected in wild-type littermate mice and the expression of C-terminal fragment of huntingtin protein was strongly inhibited.

Figure 33:
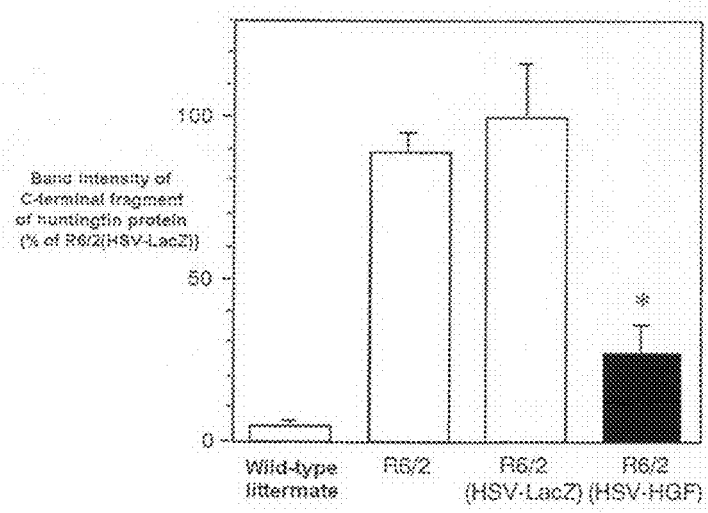
FIG. 33 shows the quantitative result of C-terminal fragment of huntingtin protein in western blot analysis. * indicates significant difference from R6/2(HSV-LacZ) mice ($p<0.05$).

The band intensity of C-terminal fragment in western blot analysis was quantified by NIH (National Institutes of Health) imaging software developed by Wayre Rasband. The result is shown in FIG. 33. As shown by the quantitative result, fragmentation into C-terminal fragment was inhibited to less than 30% in HSV-HGF-treated R6/2 mice, with the band intensity set to 100% in HSV-LacZ-treated R6/2 mice (HSV-LacZ is a control vector). This result demonstrates that HGF inhibits the processing of the gene product derived from mutant HD exon 1. The present results made it clear that HGF inhibits the onset of Huntington's disease.

Industrial Applicability

The therapeutic or onset-suppressing agent is a useful medicament for treating a polyglutamine aggregation-caused disease or suppressing the onset thereof.

The invention claimed is:

1. A method for treating a polyglutamine aggregation-caused disease or suppressing an onset thereof, comprising an administration to a mammal of HGF protein or a salt thereof,
    wherein the mammal is a mammal with a polyglutamine aggregation-caused disease or a mammal with a gene responsible for a polyglutamine aggregation-caused disease having about 30 CAG repeats or more, and
    the HGF protein or salt thereof is administered into the striatum or the spinal parenchyma, or is intrathecally administered, and
    10 µg to 50 mg of HGF protein is administered in a single dose.

2. The method according to claim 1, wherein the HGF protein represented by SEQ ID NO: 4 is administered to the mammal.

3. The method according to claim 1, wherein 1 to 25 mg of HGF protein is administered in a single dose.

4. A method for inhibiting ventricular dilatation, comprising an administration to a mammal of HGF protein or a salt thereof,
    wherein the mammal is a mammal with a polyglutamine aggregation-caused disease or a mammal with a gene responsible for a polyglutamine aggregation-caused disease having about 30 CAG repeats or more, and
    the HGF protein or salt thereof is administered into the striatum or the spinal parenchyma, or is intrathecally administered, and
    10 µg to 50 mg of HGF protein is administered in a single dose.

5. The method according to claim 4, wherein the HGF protein represented by SEQ ID NO: 4 is administered to the mammal.

6. The method according to claim 4, wherein 1 to 25 mg of HGF protein is administered in a single dose.

7. A method for inhibiting neurodegeneration or cell death dependent on a gene product responsible for a polyglutamine aggregation-caused disease, comprising an administration to a mammal of HGF protein or a salt thereof,
wherein the mammal is a mammal with a polyglutamine aggregation-caused disease or a mammal with a gene responsible for a polyglutamine aggregation-caused disease having about 30 CAG repeats or more, and
the HGF protein or salt thereof is administered into the striatum or the spinal parenchyma, or is intrathecally administered, and
10 μg to 50 mg of HGF protein is administered in a single dose.

8. The method according to claim 7, wherein the HGF protein represented by SEQ ID NO: 4 is administered to the mammal.

9. The method according to claim 7, wherein 1 to 25 mg of HGF protein is administered in a single dose.

10. A method for inhibiting caspase-3 and/or caspase-1 activation in a neuron, comprising an administration to a mammal of HGF protein or a salt thereof,
wherein the mammal is a mammal with a polyglutamine aggregation-caused disease or a mammal with a gene responsible for a polyglutamine aggregation-caused disease having about 30 CAG repeats or more, and
the HGF protein or salt thereof is administered into the striatum or the spinal parenchyma, or is intrathecally administered, and
10 μg to 50 mg of HGF protein is administered in a single dose.

11. The method according to claim 10, wherein the HGF protein represented by SEQ ID NO: 4 is administered to the mammal.

12. The method according to claim 10, wherein 1 to 25 mg of HGF protein is administered in a single dose.

13. A method for inhibiting a processing of a gene product responsible for a polyglutamine aggregation-caused disease, comprising an administration to a mammal of HGF protein or a salt thereof,
wherein the mammal is a mammal with a polyglutamine aggregation-caused disease or a mammal with a gene responsible for a polyglutamine aggregation-caused disease having about 30 CAG repeats or more, and
the HGF protein or salt thereof is administered into the striatum or the spinal parenchyma, or is intrathecally administered, and
10 μg to 50 mg of HGF protein is administered in a single dose.

14. The method according to claim 13, wherein the HGF protein represented by SEQ ID NO: 4 is administered to the mammal.

15. The method according to claim 13, wherein 1 to 25 mg of HGF protein is administered in a single dose.

* * * * *